(12) United States Patent
Rich et al.

(10) Patent No.: US 10,390,715 B2
(45) Date of Patent: Aug. 27, 2019

(54) PHOTOPLETHYSMOGRAPHY SENSORS

(71) Applicants: David Rich, Gainesville, FL (US); Richard J. Melker, Gainesville, FL (US); Andrew Kersey, Gainesville, FL (US); Matt Culen, Gainesville, FL (US)

(72) Inventors: David Rich, Gainesville, FL (US); Richard J. Melker, Gainesville, FL (US); Andrew Kersey, Gainesville, FL (US); Matt Culen, Gainesville, FL (US)

(73) Assignees: University of Florida Research Foundation, Incorporated, Gainesville, FL (US); Xhale Assurance, Inc., Gainesville, FL (US)

( * ) Notice: Subject to any disclaimer, the term of this patent is extended or adjusted under 35 U.S.C. 154(b) by 557 days.

(21) Appl. No.: 13/650,310

(22) Filed: Oct. 12, 2012

(65) Prior Publication Data

US 2014/0005557 A1    Jan. 2, 2014

Related U.S. Application Data

(60) Provisional application No. 61/666,199, filed on Jun. 29, 2012.

(51) Int. Cl.
| | |
|---|---|
| *A61B 5/0205* | (2006.01) |
| *A61B 5/024* | (2006.01) |
| *A61B 5/026* | (2006.01) |
| *A61B 5/1455* | (2006.01) |
| *A61B 5/00* | (2006.01) |
| *A61B 5/087* | (2006.01) |

(52) U.S. Cl.
CPC ........ *A61B 5/02416* (2013.01); *A61B 5/0261* (2013.01); *A61B 5/14552* (2013.01); *A61B 5/6819* (2013.01); *A61B 5/0878* (2013.01)

(58) Field of Classification Search
CPC . A61B 5/02416; A61B 5/0261; A61B 5/0878; A61B 5/14552; A61B 5/6819
See application file for complete search history.

(56) References Cited

U.S. PATENT DOCUMENTS

| | | | | |
|---|---|---|---|---|
| 4,685,464 | A | * 8/1987 | Goldberger et al. | 600/344 |
| 4,865,038 | A | 9/1989 | Rich | |
| 5,190,048 | A | * 3/1993 | Wilkinson | A61B 5/0878 600/537 |
| 5,413,102 | A | 5/1995 | Schmidt et al. | |

(Continued)

OTHER PUBLICATIONS

International Search Report dated Feb. 7, 2013, international application No. PCT/US/2012/059912.
Foreign search report for EP 16159667.1 dated Apr. 28, 2016.

*Primary Examiner* — Ruth S Smith

(57) ABSTRACT

Provided according to embodiments of the invention are photoplethysmography (PPG) sensors, systems and accessories, and methods of making and using the same. In some embodiments of the invention, the PPG sensors include a clip body that includes a first end portion and a second end portion; a flex circuit attached or adjacent to the clip body, and an elastomeric sleeve that envelops (1) at least part of the first end portion and at least part of the flex circuit attached or adjacent thereto; or (2) at least part of the second end portion and at least part of the flex circuit attached or adjacent thereto.

22 Claims, 21 Drawing Sheets

(56) References Cited

U.S. PATENT DOCUMENTS

| | | | |
|---|---|---|---|
| 5,551,423 | A | 9/1996 | Sugiura |
| 5,619,992 | A | 4/1997 | Guthrie et al. |
| 5,673,692 | A | 10/1997 | Schulze et al. |
| 5,810,724 | A * | 9/1998 | Gronvall ............... 600/323 |
| 5,817,010 | A | 10/1998 | Hibl |
| 6,115,621 | A * | 9/2000 | Chin ..................... 600/323 |
| 6,285,895 | B1 | 9/2001 | Ristolainen |
| 6,909,912 | B2 | 6/2005 | Melker et al. |
| 7,024,235 | B2 | 4/2006 | Melker et al. |
| 7,127,278 | B2 | 10/2006 | Melker et al. |
| 7,341,559 | B2 | 3/2008 | Schulz |
| 7,412,272 | B2 | 8/2008 | Medina |
| 7,608,047 | B2 * | 10/2009 | Stasz .................... 600/529 |
| 7,657,295 | B2 | 2/2010 | Coakley et al. |
| 7,785,262 | B2 * | 8/2010 | Melker et al. ......... 600/484 |
| 7,881,762 | B2 | 2/2011 | Kling et al. |
| 7,887,502 | B2 | 2/2011 | Melker et al. |
| 8,073,518 | B2 | 12/2011 | Chin |
| 8,161,971 | B2 | 4/2012 | Jaffe et al. |
| 8,229,532 | B2 | 7/2012 | Davis |
| 8,452,366 | B2 | 5/2013 | Gilland |
| 8,641,635 | B2 | 2/2014 | Melker et al. |
| 8,679,028 | B2 | 3/2014 | Melker et al. |
| 8,801,620 | B2 | 8/2014 | Melker et al. |
| 2003/0236452 | A1 * | 12/2003 | Melker et al. ......... 600/323 |
| 2006/0173247 | A1 * | 8/2006 | Medina .................. 600/301 |
| 2007/0027375 | A1 * | 2/2007 | Melker ......... A61B 5/0873 600/340 |
| 2007/0032708 | A1 * | 2/2007 | Eghbal et al. ......... 600/323 |
| 2007/0078315 | A1 * | 4/2007 | Kling et al. ........... 600/323 |
| 2007/0078317 | A1 * | 4/2007 | Matlock ................. 600/323 |
| 2008/0190436 | A1 * | 8/2008 | Jaffe et al. ........... 128/207.18 |
| 2010/0192952 | A1 * | 8/2010 | Melker ......... A61B 5/0261 128/204.23 |
| 2011/0028811 | A1 * | 2/2011 | Kiani et al. ........... 600/323 |
| 2013/0276785 | A1 | 10/2013 | Melker et al. |
| 2013/0296823 | A1 | 11/2013 | Melker et al. |

* cited by examiner

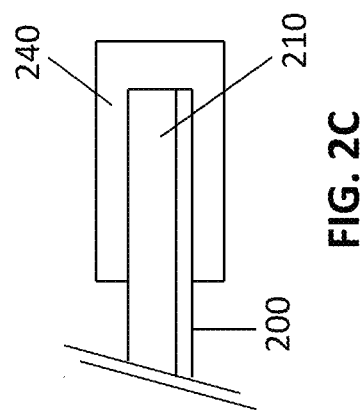
FIG. 2C
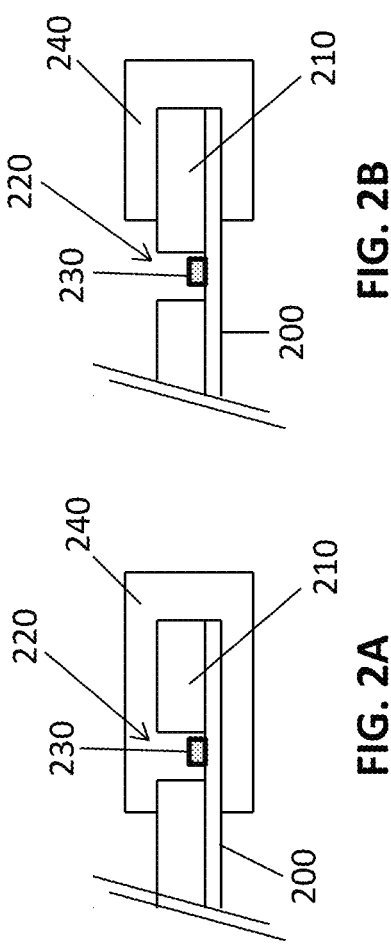
FIG. 2B
FIG. 2A
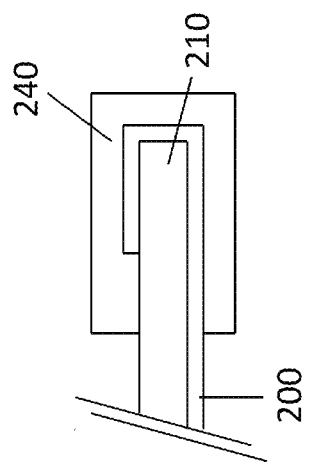
FIG. 2F
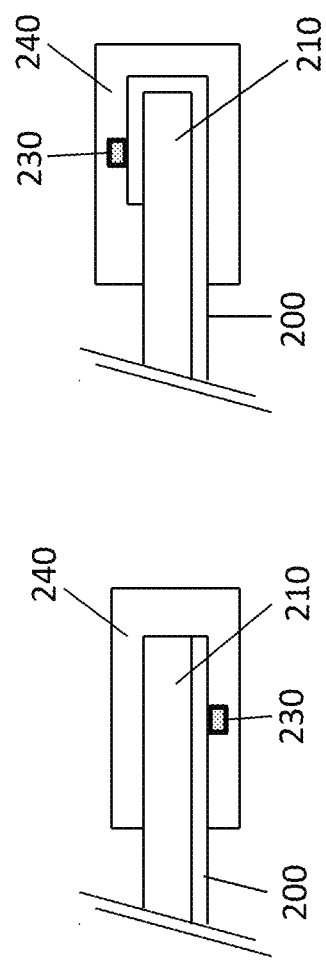
FIG. 2E
FIG. 2D

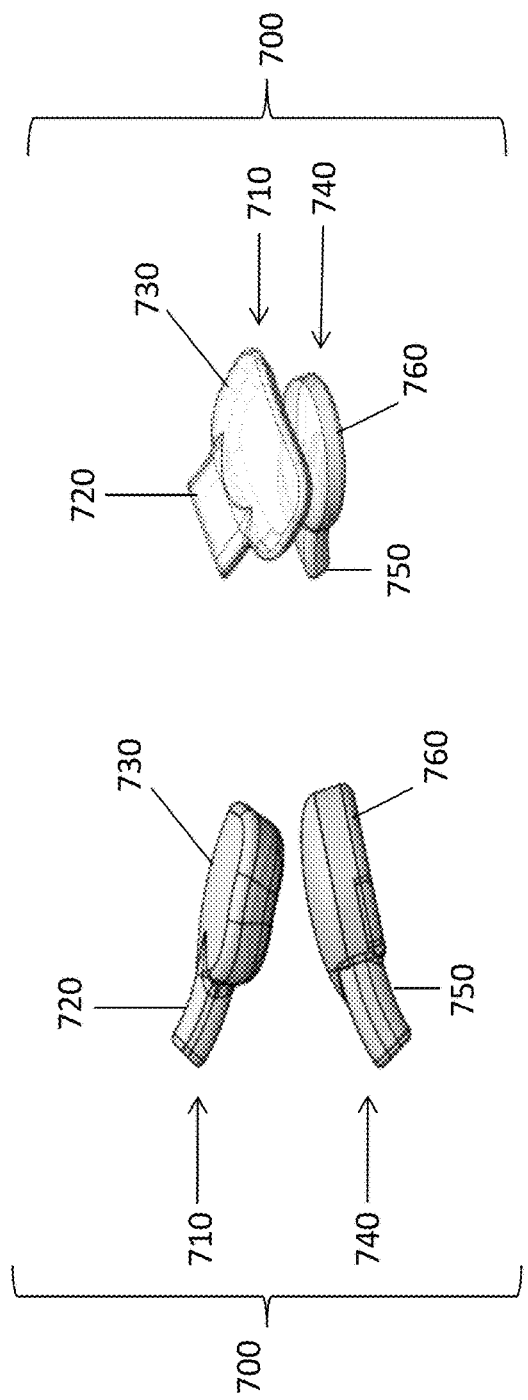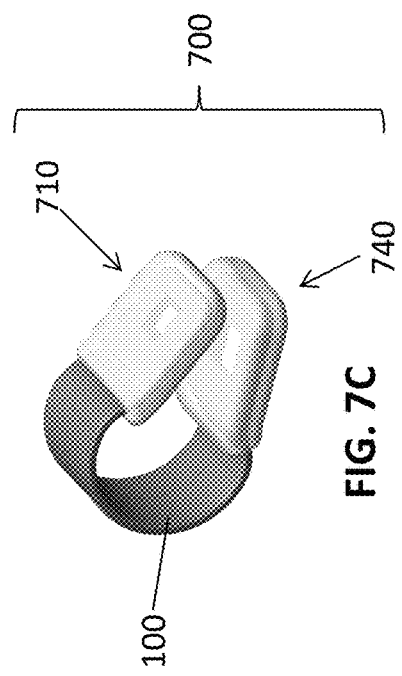
FIG. 7A
FIG. 7B
FIG. 7C

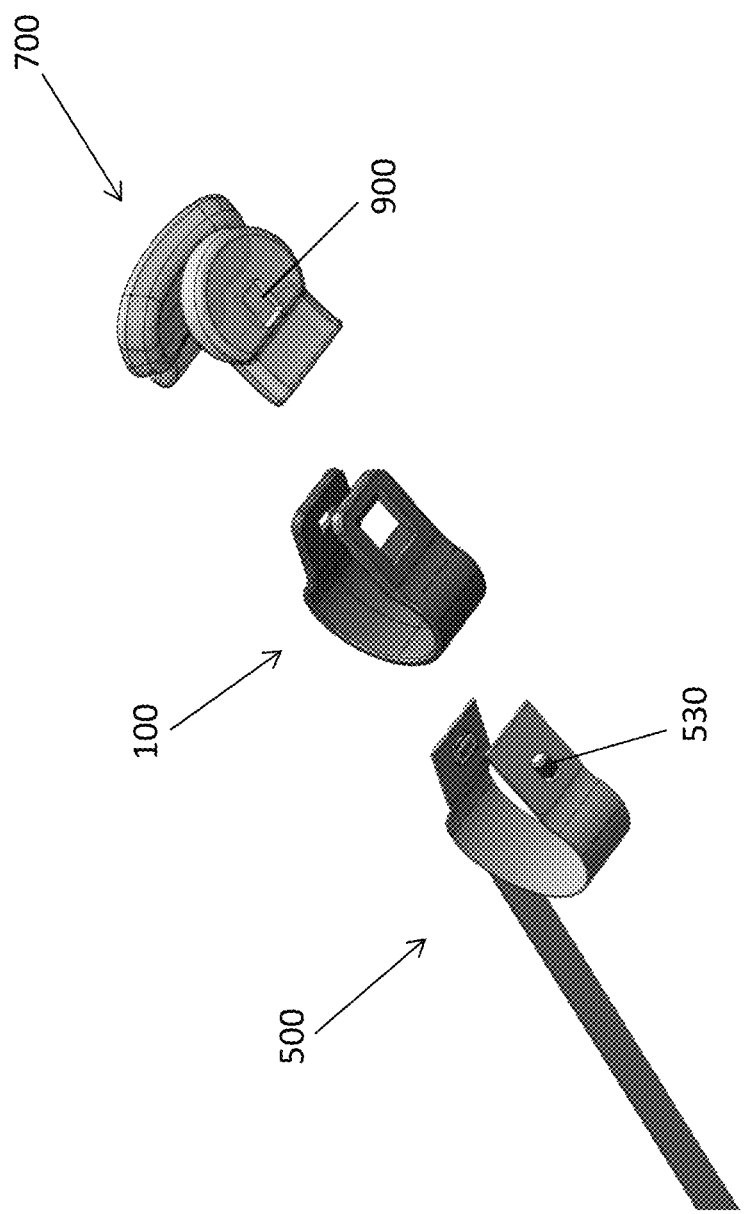

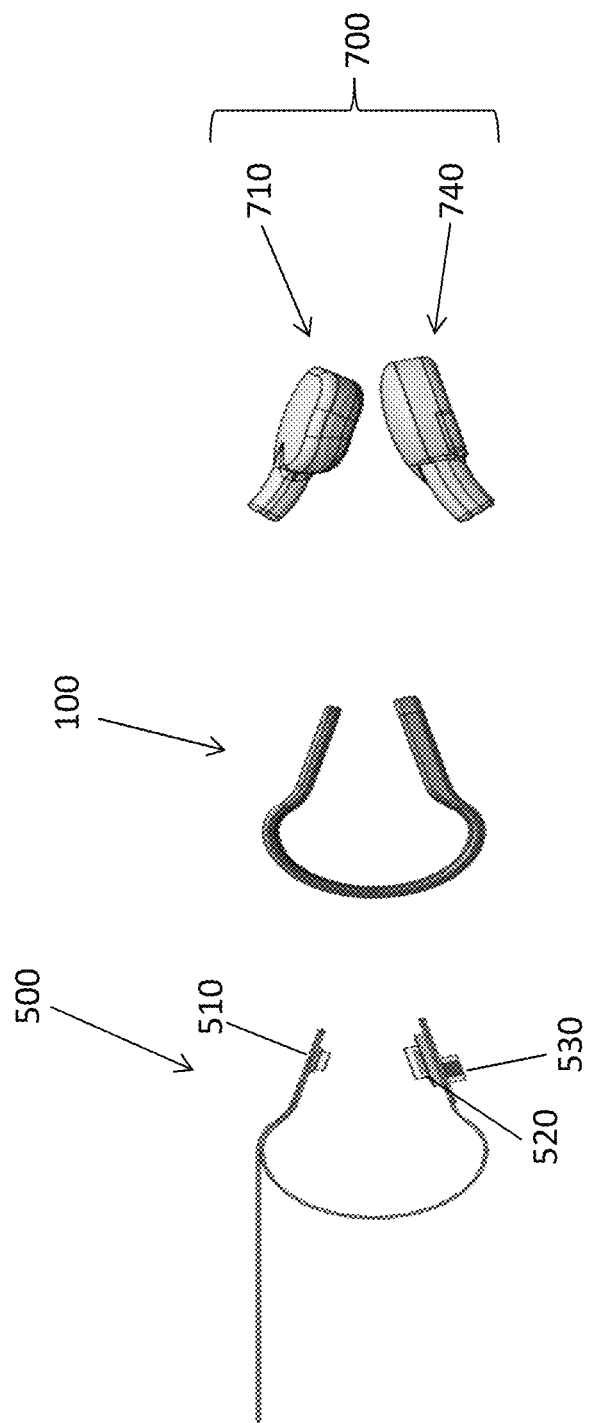

PHOTOPLETHYSMOGRAPHY SENSORS

CROSS-REFERENCE TO RELATED APPLICATIONS

This application claims the benefit of U.S. Provisional Application No. 61/666,199, filed Jun. 29, 2012, the contents of which are incorporated herein by reference in their entirety.

FIELD OF THE INVENTION

The present invention relates to biological sensors, and in particular, to photoplethysmography sensors. The present invention also relates to systems and devices for use with photoplethysmography sensors, as well as methods of using and manufacturing photoplethysmography sensors.

BACKGROUND OF THE INVENTION

Photoplethysmography, or "PPG", is an optical technique for detecting blood volume changes in a tissue. In this technique, one or more emitters are used to direct light at a tissue and one or more detectors are used to detect the light that is transmitted through the tissue ("transmissive PPG") or reflected by the tissue ("reflectance PPG"). The volume of blood, or perfusion, of the tissue affects the amount of light that is transmitted or reflected. Thus, the PPG signal may vary with changes in the perfusion of the tissue.

The blood volume in a tissue changes with each heartbeat, and so the PPG signal also varies with each heartbeat. Traditionally, this component of the PPG signal is referred to as the "AC component" component of the signal, and is also often referred to as the "pulsatile component." Blood volume is also affected by other physiological processes in the body, including respiration, venous blood volume, sympathetic and parasympathetic tone and certain pathologies. The changes in the PPG signal due to these and other physiological processes, along with changes in the PPG signal due to noise caused by non-physiological processes such as ambient light and bodily movement, have traditionally been referred to collectively as the "DC component."

The present inventors have recently extracted specific parameters from the DC component, leaving the AC component signal to be used for monitoring traditional pulse oximetry physiological parameters, such as blood oxygen saturation and heart rate. Traditional sites for monitoring PPG, such as fingers and toes, generally provide a relatively small PPG signal, and the quality of this signal may be negatively impacted by sympathetic innervation in these tissue sites. Thus, the DC component signal from traditional peripheral sites may not be of sufficient strength and quality to effectively separate out the signals from different physiological processes.

The nasal alar region has recently been shown by the inventors to provide a very large PPG signal relative to other sites of the body, including the fingers, toes and ears, and a relatively high quality signal due to its lack of sympathetic innervation. The improved PPG signal at the nasal alar site has allowed for a number of physiological parameters, including respiration rate, respiratory effort and venous capacitance to be effectively extracted from the DC signal. Examples of patents and applications that describe the use the nasal alar site to obtain PPG signals, as well as a description of parameters and physiological processes that may be extracted from such signals, include U.S. Pat. Nos. 6,909,912; 7,127,278; 7,024,235; 7,785,262; 7,887,502 and 8,161,971, the entire contents of each of which are incorporated herein by reference in their entirety.

Thus, new devices, systems and methods for PPG monitoring at the nasal alar site may be desirable. Furthermore, new devices, systems and methods for PPG monitoring generally may also be advantageous.

SUMMARY OF THE INVENTION

Provided according to embodiments of the present invention are photoplethysmography (PPG) sensors that include a sensor body, a flex circuit attached or adjacent to the sensor body, and an elastomeric sleeve that envelops part of the sensor body and the flex circuit attached or adjacent thereto. The flex circuit provides electronic components, such as an emitter and/or a detector, to the sensor. In some embodiments of the invention, one or more elastomeric sleeve(s) compressively envelop the sensor body and the flex circuit, which may bind the sensor body and flex circuit and may reduce or eliminate the need for the use of adhesives in the sensor. In particular embodiments, no adhesive is present between the clip body and the flex circuit, between the clip body and the elastomeric sleeve and/or between the flex circuit and the elastomeric sleeve.

In some embodiments of the invention, provided are PPG sensors that include a clip body that includes a first end portion and a second end portion; a flex circuit attached or adjacent to the clip body, and an elastomeric sleeve that envelops (1) at least part of the first end portion and at least part of the flex circuit attached or adjacent thereto; or (2) at least part of the second end portion and at least part of the flex circuit attached or adjacent thereto. In some embodiments, the PPG sensor is configured to secure to the nasal alar region of the nose. To this end, in some embodiments, the first end portion is configured to secure to an external tissue of a nasal alar, and the second end portion is configured to secure to an internal tissue of the nasal alar. The PPG sensors may also include other physiological monitors such as secondary respiration detectors.

In some embodiments of the invention, provided are PPG sensors that include a molded polymer clip that includes (a) a first end portion configured to secure onto an external tissue of a nasal alar and (b) a second end portion configured to secure onto an internal tissue of the nasal alar.

Also provided according to embodiments of the invention are systems for monitoring a subject that include a PPG sensor according to an embodiment of the invention and a computer communicatingly connected to the PPG sensor. The computer may be configured to process the signals from the PPG sensor to measure or monitor physiological processes. For example, the system may process the PPG signals to monitor blood oxygen saturation levels, respiration and/or blood flow.

Also provided according to embodiments of the present invention are methods of manufacturing a PPG sensor. Such methods include inserting an end portion of a sensor body and a part of a flex circuit attached or adjacent to the sensor body into an elastomeric sleeve. In some embodiments, the elastomeric sleeve is configured to bind the flex circuit and the sensor body together. Methods of manufacturing PPG sensors also include joining a sensor body and a flex circuit, and overmolding a part of the sensor body and a part of the flex circuit attached or adjacent thereto with an elastomeric material to form an elastomeric sleeve that envelops the part of the sensor body and the part of the flex circuit attached or adjacent thereto.

Further provided according to embodiments of the invention are applicators for placing a clip plethysmography sensor onto a patient. Such devices may include a first device arm configured to secure to a first end portion of the PPG sensor; and a second device arm configured to secure to a second end portion of the PPG sensor, such that the device body is configured to separate the first device arm from the second device arm. Also provided are kits for PPG monitoring that include a PPG sensor that includes a clip body and an applicator according to an embodiment of the invention.

BRIEF DESCRIPTION OF THE DRAWINGS

The following drawings are provided to illustrate various aspects of the present inventive concept and are not intended to limit the scope of the present invention unless specified herein.

FIG. 1A depicts a clip body having a rounded shape; FIG. 1B depicts a clip body having a squared off shape and first and second end portions of substantially equal length; FIG. 1C depicts a clip body having first and second end portions of different lengths; and FIG. 1D depicts an irregularly shaped clip body.

FIG. 2A-2F are cross-sectional illustrations showing exemplary configurations of a sensor body and a flex circuit enveloped within an elastomeric sleeve.

FIG. 7A shows a side-view of a pair of elastomeric sleeves according to an embodiment of the invention. FIG. 7B shows a view looking down on the same pair of elastomeric sleeves.

FIG. 7C shows a pair of elastomeric sleeves, as shown enveloping end portions of a clip body, according to another embodiment of the invention.

FIG. 9 depicts the clip body, flex circuit and elastomeric sleeves from FIG. 8, as shown from below.

FIG. 10 depicts the clip body, flex circuit and elastomeric sleeves from FIG. 8, as shown from the side.

DETAILED DESCRIPTION OF EMBODIMENTS OF THE INVENTION

Figure 1A:
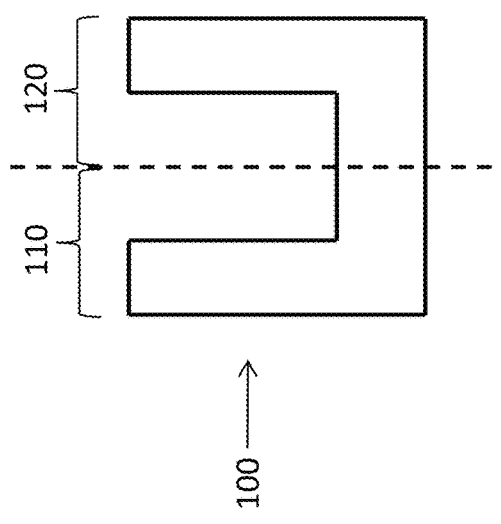
FIGS. 1A-1D are cross-sectional illustrations showing examples of different types of clip body configurations.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "on" or "adjacent" to another element, it can be directly on or directly adjacent to the other element or intervening elements may also be present. In contrast, when an element is referred to as being "directly on" or "directly adjacent" to another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. may be used herein to describe various elements, these elements should not be limited by these terms. These terms are only used to distinguish one element from another. Thus, a first element discussed below could be termed a second element without departing from the teachings of the present invention.

Embodiments of the present invention are described herein with reference to schematic illustrations of idealized embodiments of the present invention. As such, variations from the shapes of the illustrations as a result, for example, of manufacturing techniques and/or tolerances, are to be expected.

Photoplethysmography Sensors

Provided according to embodiments of the present invention are photoplethysmography (PPG) sensors. Such sensors include a sensor body, a flexible electronic circuit (also referred to as "flex circuit") attached or adjacent thereto, and an elastomeric sleeve that envelops at least part of the sensor body and at least part of the flex circuit attached or adjacent to the sensor body. In some embodiments, the elastomeric sleeve may act to bind the sensor body and the flex circuit, which may reduce or eliminate the need for adhesives in the sensors, may simplify the manufacturing process and, in some cases, may decrease manufacturing costs. The elastomeric sleeves may also be useful for patient comfort and for securing of the PPG sensor to the wearer (also referred to herein as the "subject" or "patient").

(1) The Sensor Body

The sensor body refers to a structural body that is configured to support the flex circuit and allow for the sensor to secure to a tissue site. The term "secure" means to attach sufficiently to the tissue site to allow for a suitable PPG signal to be generated. In some cases, the sensor body is configured to secure onto a tissue site such that no additional support is necessary to allow for a suitable PPG signal to be reliably generated. However, in some cases, the sensor body may be secured with the aid of an external support, for example, an additional structural support, a wire or cord, or an adhesive product such as tape. Such supports may be desirable to stabilize the sensor to prevent against signal loss, for example, due to the patient's movement, or due to movement (e.g., jostling, pulling, pushing) of the sensor or a cable attached thereto.

The sensor body may be formed of any suitable material, including but not limited to, metals, polymers, polymer blends, and combinations thereof. The type of metal, polymer or polymer blend used depends on the type of PPG sensor and its intended use. As such, many thermoplastic and thermoset polymers may be suitable for use in the sensor body. However, in particular embodiments, the sensor body includes polycarbonate, acetal, nylon, polyester, or a combination thereof. Many metals may also be suitable for use in the sensor body, and in some embodiments, malleable metals, such aluminum, may be desirable. In particular embodiments, the sensor body is a molded article, such as a molded polymer article or a molded metallic article. In a particular embodiment, the material of the sensor body and/or clip is highly opaque and non-tranmissive of light in the visible and IR spectrums to prevent the light from an emitter from reaching the detector without first passing through tissue at the measurement site.

The sensor body may be composed of smaller pieces, which are assembled to form the sensor body, but in some embodiments, the sensor body is a single molded article. The use of a single molded article eliminates the need for assembly of the sensor body, and so may increase manufacturing efficiency and/or decrease manufacturing costs. In some embodiments, the sensor body may be flexible and/or malleable. In particular embodiments, the flexural modulus of the material that forms the sensor body is in a range of 300,000 to 350,000 psi, and in some cases, in a range of 350,000 to 450,000 psi.

Figure 1B:
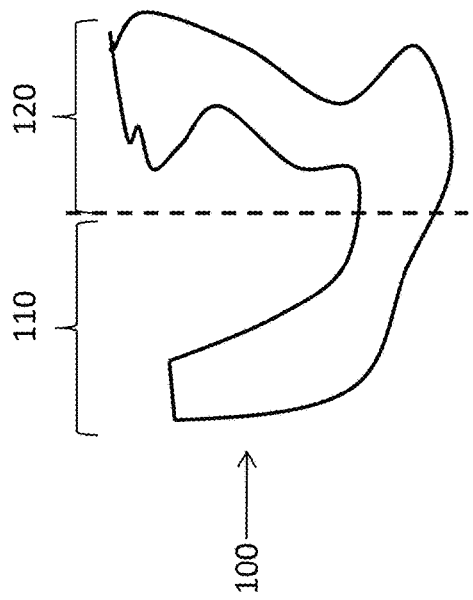
Figure 1C:
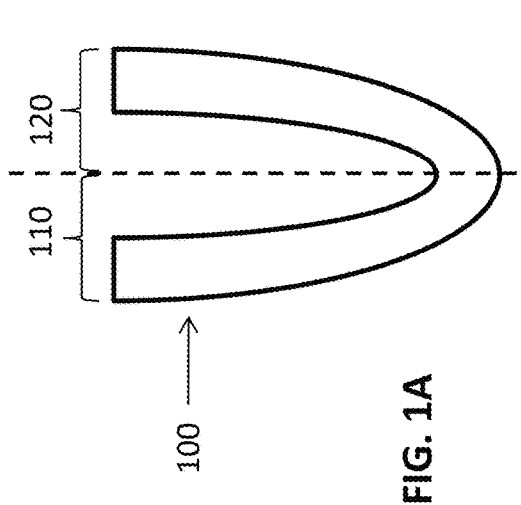
Figure 1D:
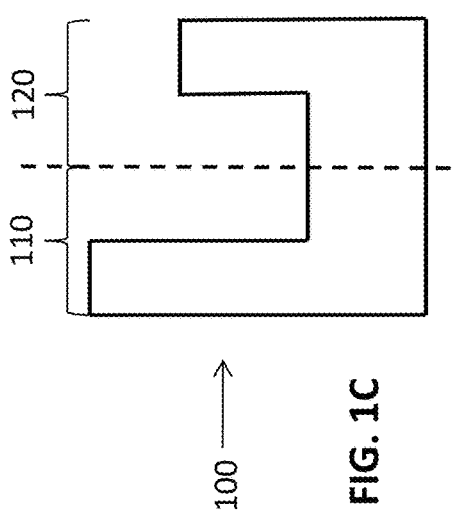

In certain embodiments of the invention, the sensor body is a clip, and so will be referred to herein as a "clip body". The term "clip body" refers to a device that has at least two end portions that grasp and secure to a tissue site. The clip body may be configured in a number of shapes, including, for example, "U-shaped" or "C-shaped", squared, rounded, pointed, regular or irregular shaped. FIGS. 1A-1D provide coarse cross-sectional illustrations of a type of clip body 100 that includes a first end portion 110 and a second end portion 120. As shown in FIG. 1A, the clip body 100 may be curved, but other configurations may be suitable or desirable. As shown in FIG. 1B, in some embodiments, the clip body 100 may have a square or rectangular shape. FIG. 1B also shows a first end portion 110 and a second end portion 120 that are the same or substantially the same length. However, in other embodiments, the end portions may be of different lengths and/or different shapes. FIG. 1C depicts a clip body 100 that has a first end portion 110 and a second end portion 120 having different lengths. In some embodiments, a first end portion 110 and/or a second end portion 120 of the clip body 100 may include a concave portion and/or convex portion (not shown). As shown in FIG. 1D, the clip body may also be irregularly shaped. In particular embodiments, the clip body 100 may be configured to conform a curvature of a particular tissue (not shown).

Although FIGS. 1A-1D show a particular boundary between the first and second end portions, such as halfway or at a "central point" between the two ends of the clip body, the exact location of the boundary is not critical. However, in general, a first end portion grasps one side of a tissue and a second end portion grasps the other side of the tissue. For example, in FIG. 1C, the end portions have two different lengths, but the clip body may be configured such that a longer end portion is meant to grasp one side of a tissue, while the shorter end is meant to grasp the other side of the tissue. As an additional example, for the irregular clip body 100 in FIG. 1D, while it is clear that there are two end portions, there is no clear central point. Thus, any and all reasonable apportionments of the first and second end portions of the clip body are envisioned.

In some cases, there may be additional structural, functional or design elements in or on the clip body, and any of the materials and features described herein with respect to the sensor body are also applicable to the clip body. For example, the clip body may have additional arms or extensions, and so may have additional end portions. The clip body may also be configured so that it can retract or extend to facilitate adjustment or placement of the sensor.

In some embodiments of the invention, the sensor body includes at least one aperture defined therein. As used herein, the term "aperture" is meant to refer to an opening in the sensor body that is sufficient to allow light to pass through, and includes holes, slits, slots or openings of any shape that are enclosed by the sensor body. The apertures may be of uniform area or may be stepped, tapered or otherwise non-uniform to facilitate alignment of mating elements or aid in manufacturing or fabrication. The aperture(s) may also be present in any part of the sensor body and two or more apertures may be spaced closely or farther apart, or in any other suitable formation. In some embodiments, the sensor body does not include any apertures, and so is a solid, continuous article. However, in some cases, the sensor body may have irregular edges and/or may include, for example, notches, indentations, and the like.

With respect to a clip body, one or more apertures may be present in the first end portion and/or the second end portion. In particular embodiments, the sensor body is a clip body that has at least one aperture in the first end portion and at least one aperture in the second end portion. In other particular embodiments, the clip body has at least one aperture on one of the end portions, but the other end portion does not include an aperture.

The clip body, in some cases, may also incorporate grips, such as those that extend away from the first and second end portions, that provide squeezing surfaces in the manner of a clothespin that cause the clip to open thereby facilitating attachment to the alar. However, in some cases, such grips are not necessary, for example, when an applicator or device for placing the sensor at a body site is used. Clip bodies that incorporate grips and applicators for applying sensors are described below in more detail with respect to nasal alar sensors.

(2) The Flex Circuit

The flex circuit provides at least one electronic component to the sensor, and any suitable electronic component may be included in or on the flex circuit. When a flex circuit is said to "include" or "comprise" an electronic component, it is meant that the electronic component is within the flex circuit or on a surface of the flex circuit. In order to secure sufficiently to the tissue, the flex circuit may be attached to or adjacent to the sensor body. The term "attached" includes mechanical attachment, e.g., via hooks or fasteners, or chemical attachment, e.g., via adhesives. The term "adjacent" means that the flex circuit is next to and/or touching the sensor body, but not actually attached to the sensor body. As used herein, the term "joined" will refer to both attaching the flex circuit to the clip body and placing the flex circuit adjacent to the clip body. In some embodiments, one or more elastomeric sleeves sufficiently bind the sensor body and the flex circuit together so that the sensor body and the flex circuit need not be attached to each other. Thus, in some embodiments, no adhesive is present between the flex circuit and the clip body, between the clip body and the elastomeric sleeve and/or between the flex circuit and the elastomeric sleeve.

The flex circuit includes one or more components that emit light, and such components will be referred to herein as "emitters." As used herein, the term "light" is used generically to refer to electromagnetic radiation, and so the term includes, for example, visible, infrared and ultraviolet radiation. Any suitable type of emitter may be used, but in some embodiments, the emitter is a light-emitting diode (LED). In particular embodiments, a first emitter on the flex circuit emits light at a first wavelength, and a second emitter on the flex circuit emits light at a second wavelength. For example, a sensor that may be used to measure blood oxygen saturation levels may include a first emitter that emits light in the visible range and a second emitter that emits light in the infrared range. In some cases, a single emitter may emit light at a first wavelength and a second wavelength. One or more photodetectors, also referred to as "detectors", are also included on the flex circuit. The detector is configured to detect light from an emitter, and this detected light generates a PPG signal. Any suitable photodetector may be used. However, examples of photodetectors include photodiodes, photoresistors, phototransistors, light to digital converters, and the like.

While any suitable type of flex circuit may be used, in some embodiments, the flex circuit is a single electrically conductive layer, housed in insulative plastic, which has all of the electronic components on the same side of the circuit. Furthermore, in particular embodiments, the flex circuit includes a moisture protective conformal coating.

Electronic components that provide additional physiological monitoring to the sensor may also be included on the flex circuit. Examples of physiological monitoring components that may be included on the flex circuit include respiration detectors such as thermistors, thermocouples, resistance temperature detectors (RTDs), moisture detectors, capnometers, microphones, pressure sensors, nasal airway flow detectors, and vibration detectors. Other physiological monitoring components that may be included on the flex circuit include oxygen sensors, pH sensors, and sensors for identifying and/or measuring particular compounds in the nasal airflow.

In some embodiments, an electronic component for wireless communication may be included on the flex circuit. Any suitable wireless communication component may be included on the flex circuit, but in some embodiments, a Bluetooth®, WiFi and/or infrared technology may be used. Such electronic components may communicate with a receiver apparatus so that PPG signals acquired by the sensor may be transmitted wirelessly to a control and/or signal processing unit.

In some embodiments, the electronic components are mounted on the flex circuit, and this may be achieved by any suitable technique, including, for example, via soldering and/or adhesives. The electronic components may also be mounted in any suitable configuration and on any part of the flex circuit. For example, in some cases, an emitter may be mounted on a first end portion of the flex circuit and the detector may be mounted on a second end portion of the flex circuit. Furthermore, in some embodiments, an emitter and a detector may be on the same end portion of the flex circuit, and in some cases, may be adjacent to each other. In some embodiments, the electronic components are "through-hole components" or "chip on board" components, so that the electronic components are not mounted on the surface of the flex circuit but are otherwise incorporated into the flex circuit. It is also to be understood that while the flex circuit is included to introduce electronic components to the sensor, in some embodiments, electronic components may also be present on other portions of the sensor, including the sensor body and/or the elastomeric sleeve.

In some embodiments, the flex circuit includes or is attached to a wire or cable for transmitting or communicating signals from the sensor to a computer or other analysis/processing equipment. In some cases, a portion of flex circuit itself may be considered part of the cabling. The flex circuit may also include a connector for coupling the flex circuit to a wire, cable or another electronic device. Any suitable wire, cable or other electrical connector may be used as the connector. In other embodiments of the invention, the PPG signals may be transmitted wirelessly, and so no wire or cabling is needed, and thus, the flex circuit may not include any cables or connectors.

(3) The Elastomeric Sleeve

The "elastomeric sleeve" is an elastomeric material that envelops part of the sensor body and part of the flex circuit attached or adjacent thereto. The sleeve may be formed from more than one piece of elastomeric material, but in some embodiments, the sleeve may be a molded elastomeric sleeve, and as such, the sleeve may be a single molded elastomeric article.

The term "elastomeric" is meant to include any polymer or polymer blend that exhibits elasticity or viscoelasticity. Thus, both thermoplastic and thermoset polymers may be used, provided that they are elastomeric. Examples of elastomeric polymers that may be used in some embodiments include some types of silicones, natural rubbers, polyurethanes, block copolymers, including styrenic block copolymers, and PVC. In some embodiments of the invention, the elastomeric sleeve is configured to aid in securing the PPG sensor to the tissue. As such, in some cases, the elastomeric sleeve is formed from material that has a relatively high coefficient of friction with respect to skin. In some embodiments, the coefficient of friction is in a range of 0.35 to 1.3, and in particular embodiments, in a range of 0.40 to 0.80, with respect to skin. The softness of the elastomeric sleeve may also increase friction, while providing comfort to the subject, thus aiding in securing the sensor to the tissue. As such, in some cases, the elastomeric sleeve is relatively soft. For example, in some cases, the Shore A durometer may be in a range of 30 and 80, and in particular embodiments, the Shore A durometer is about 40.

In some embodiments, the surface of the elastomeric sleeve may also be smooth and/or polished, which may aid in securing the PPG sensor to the tissue and/or increase the comfort of the wearer. The smoothness may also adjust the coefficient of friction to a desired value. Indeed, the inventors have found that in some cases, if the portion of the elastomeric sleeve that contacts body tissue is smooth, the coefficient of friction is increased and the sensor more securely attaches to the tissue. The inside portion of the elastomeric sleeves may also be smooth, which may also increase the coefficient of friction between the elastomeric sleeve and/or the sensor body and the flex circuit, or otherwise facilitate binding of the sensor body and the flex circuit within the elastomeric sleeve.

In particular embodiments, the elastomeric sleeve may contain within or be treated with lubricants or coatings to produce a highly lubricous surface to reduce the coefficient of friction thereby aiding in sliding the sensor onto the tissue at the application site. Such lubricants or coatings could be permanent or temporary in nature. As such, in some cases, the lubricants or coatings may evaporate or otherwise disappear from the elastomeric sleeves, for example, such as with volatile organic compound. In some cases, a lubricated elastomeric sleeve may secure to a tissue site, and the evaporation of the lubricant may further create a "sticky" surface that provides desirable adhesion. In the case of permanent lubricants, additives in the elastomeric material or coatings may aid in application, repositioning and/or ease removal, but may require secondary taping systems to hold the sensor in place. Examples of permanent lubricants or coatings include Teflon, Parylene and waxes.

In some embodiments, the elastomeric sleeve includes a transparent polymer, and in some cases, only part of the elastomeric sleeve is transparent. In some cases, part of the elastomeric sleeve is transparent and so configured to transmit light through the sleeve, while part of the elastomeric sleeve is semi-transparent or opaque. Such a configuration may be useful to minimize light escaping from the sensor and may also decrease the amount of ambient light that is introduced into the sensor. This may be beneficial for the efficiency and/or accuracy of the sensor and may also reduce or eliminate the escape of light that may be a nuisance to the wearer. In a particular embodiment, a transparent window is molded into an opaque body, and so light from an emitter may pass through the transparent window of the sleeve but may not significantly disperse or escape from the sensor due to the opaque sleeve surrounding the window. In another embodiment, a part of the elastomeric sleeve is painted or otherwise coated to provide the desired opacity. Adhesive patches may also be applied to the elastomeric sensor to minimize or prevent light from the emitter exiting the sensor and/or to minimize or prevent ambient light from reaching the detector. In some cases, the elastomeric sleeves may also scatter or diffuse the light from the emitter. In particular, when a "pinpoint" LED light source is used, the scattering or diffusing of light may be beneficial. For example, when two pinpoint LED light sources are directly next to one another, the scattering or diffusing of the light by the elastomeric sleeves may allow for the light from each emitter to travel through the same tissue.

The size of the elastomeric sleeve may vary according to the desired use and configuration. As with the sensor body, the elastomeric sleeve can be formed to include a convex and/or concave surface, and in some cases, may be formed to conform to the curvature of the tissue on which it is configured to be placed. The elastomeric sleeve may also have a rounded, squared or other shape. In particular embodiments, the elastomeric sleeve is shaped so that it generally follows the contours of the clip body. In some embodiments, a small portion of the sensor may be enveloped by the elastomeric sleeve, and in other embodiments, a large portion of the sensor may be enveloped by the elastomeric sleeve. In some embodiments, the elastomeric sleeve has sufficient length to cover an emitter and/or detector on the flex circuit. In some embodiments, the elastomeric sleeve has sufficient length to bind the sensor body and the flex circuit together. The elastomeric sleeve may have any suitable width, but should be sufficiently wide to allow for the sensor body and the flex circuit to be inserted therein.

While the elastomeric sleeve may be configured to bind the sensor body and the flex circuit together, the elastomeric sleeves may also provide additional benefits, such as providing cushioning to the tissue on which it is to be secured, and facilitating securing of the PPG sensor to the tissue. In some cases, the sensor body and the flex circuit attached or adjacent thereto may be compressively enveloped by the elastomeric sleeve, and so create an interference fit. As described above, this may decrease or eliminate the need for the use of adhesives in the sensor. In particular embodiments, two or more elastomeric sleeves are used to bind the sensor body and the flex circuit attached or adjacent thereto. For example, with the clip body, in some embodiments, a first elastomeric sleeve envelops a first end portion of the clip body and a second elastomeric sleeve envelops a second end portion of the clip body.

(4) General Considerations

It should be understood that the flex circuit and the sensor body may be present in a number of different configurations within the elastomeric sleeve, and any suitable configuration may be used. As an example, referring to FIG. 2A, the flex circuit portion 200 may be attached or adjacent to a sensor body portion 210 having an aperture 220, such that an electronic component 230, such as an emitter, is within or adjacent to the aperture 220 in the sensor body portion 210. An elastomeric sleeve 240 may envelop part of the sensor body portion 210 and the flex circuit portion 200 attached or adjacent thereto, and in this case, may also envelope the aperture 220 and the electronic component 230 as well. Referring to FIG. 2B, in some embodiments, the elastomeric sleeve 240 does not envelop the electronic component 230. As another example, referring to FIG. 2C, there may not be an aperture 220 in an enveloped portion of the sensor body portion 210 and the flex circuit portion 200. In some cases, the sensor body portion 210 may be attached or adjacent to the flex circuit portion 200, but no electronic component 230 is present in the particular end portion. Referring to FIG. 2D, an electronic component 230 may also be, for example, on a surface 250 of the flex circuit 200 that is not facing the sensor body portion 210. As a final example, referring to FIGS. 2E and 2F, the flex circuit portion 200 may also wrap around the sensor body portion 210 before being enveloped by the elastomeric sleeve 240, and may include (2E) or not include (2F) and electronic component 230 thereon.

According to some embodiments of the invention, the PPG sensor is partially or completely disposable. As such, the sensor may be used for a single use or for more than one use, for example, 2-10 uses, including 2, 3, 4 or 5 uses. In such cases, the sensor body, the flex circuit and the elastomeric sleeve may be formed from a sufficiently inexpensive material that also meets safety and performance standards. In addition, the relatively few assembly steps also decrease production costs and may allow for the partial or complete disposability of the sensor. The disposability of the sensor may be advantageous in some cases because it may decrease or eliminate the need for cleaning and disinfection, which may, in turn, improve the ease of use for medical personnel.

(5) Methods of Making PPG Sensors

Any suitable method of making the PPG sensors described herein may be used. However, in some embodiments of the invention, manufacturing a PPG sensor includes inserting an end portion of a sensor body and a part of a flex circuit attached or adjacent to the sensor body into an elastomeric sleeve. In some embodiments, the elastomeric sleeve may be configured to compressively envelope or bind the flex circuit and the sensor body together to create an interference fit.

A flex circuit may be purchased in a condition suitable for inclusion in the PPG sensors described herein, but in some cases, the flex circuit is first prepared by mounting the desired electronic components on the appropriate sections of the flex circuit. Surface mounting of electronic components onto flex circuits is known in the art, and so any suitable technique, including soldering or adhesives, may be used. The flex circuit may also be further prepared by introducing a connector onto the flex circuit, such as, for example, soldering pads on the flex circuit for use as a connector. In order to have the electronic components in the proper location for joining with the sensor body, the flex circuit may also be folded and secured, such as via an adhesive, in a folded configuration.

The sensor body may also be purchased or may be manufactured, and any suitable method of making the sensor body may be used. In some embodiments, the sensor body is manufactured by inserting a fluid monomer, polymer and/or polymer blend into a mold, and solidifying the monomer or polymers. For example, a monomer may be polymerized in order to form a solid sensor body. In other embodiments, a melted or softened polymer or polymer blend is inserted into a mold and the temperature of the material is lowered until the polymer material solidifies. Such methods are known to the skilled artisan, and any technique for creating molded polymer articles may be used. The elastomeric sleeve may also be formed by the same or similar techniques, although the polymers or polymer blends used for the sensor body may be different from those used to form the elastomeric sleeve.

The sensor body and the flex circuit may next be joined, such as via an attachment mechanism or by simply placing the two components next to or touching one another, so that the flex circuit is attached or adjacent to the sensor body. In particular, the flex circuit may be wrapped around the sensor body in preparation for insertion into the elastomeric sleeves. In particular cases, an electronic component, such as an emitter or a detector, may be placed within or adjacent to an aperture in the sensor body. Two or more electronic components may also be placed within or adjacent to a single aperture.

Next, an end portion of the sensor body and a part of the flex circuit attached or adjacent thereto may be inserted into an elastomeric sleeve. In some embodiments, a lubricant is used to facilitate insertion of the sensor body and flex circuit into the elastomeric sleeve. The lubricant may be placed on the sensor body and/or the flex circuit. Additionally or alternatively, the lubricant may be placed within the elastomeric sleeve prior to insertion of the sensor body and flex circuit. Any suitable lubricant may be used, but in some cases, the lubricant is a volatile organic compound such as an alcohol. The evaporation of the volatile organic compound may allow for the elastomeric sleeves to securely grip the sensor body and flex circuit, thus binding the flex circuit and sensor body together. A swelling agent may also be used to facilitate the elastomeric sleeve's binding of the flex circuit and clip body. In some cases, the lubricant may also be a swelling agent. One or more additional end portions of the sensor body, and the flex circuit attached or adjacent thereto, may also be inserted into one or more additional elastomeric sleeves. In particular embodiments, a first end portion of the sensor body and the flex circuit attached or adjacent thereto is inserted into a first elastomeric sleeve and a second end portion of the sensor body and the flex circuit attached or adjacent thereto may be inserted into a second elastomeric sleeve.

While, in general, the sensor body and the flex circuit attached or adjacent thereto are inserted into the elastomeric sleeve(s), in some embodiments, the elastomeric sleeves can be overmolded onto the flex circuit and sensor body. Overmolding techniques are known in the art and any known technique suitable for this application can be used to produce a sensor body according to an embodiment of the invention.

As the skilled artisan will appreciate, additional steps may be included in the manufacture of PPG sensors according to embodiments of the invention. Furthermore, the steps described above may be performed in any suitable order. A particular method of making a nasal alar PPG sensor according to an embodiment of the invention will be described in detail below.

Nasal Alar PPG Sensors and Applicators

Figure 3:
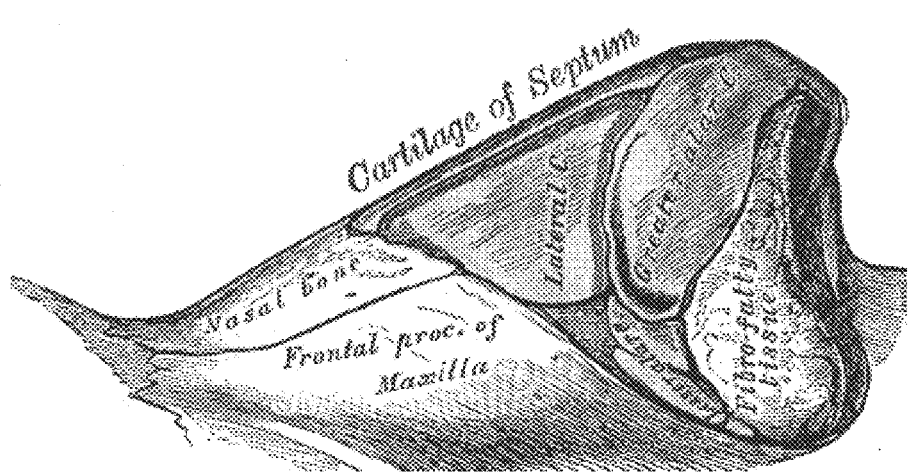
FIG. 3 is an illustration of the nose that identifies the nasal alar region.
Figure 4A:
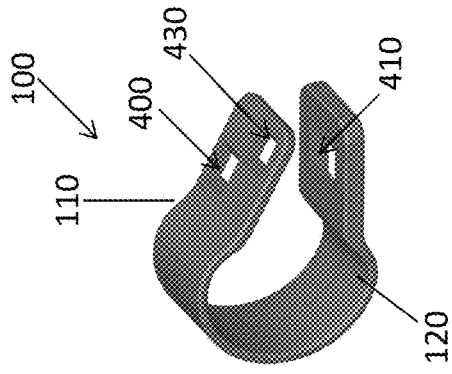
FIG. 4A-4F show a variety of clip bodies that may be included in nasal alar sensors according to embodiments of the invention.
Figure 4B:
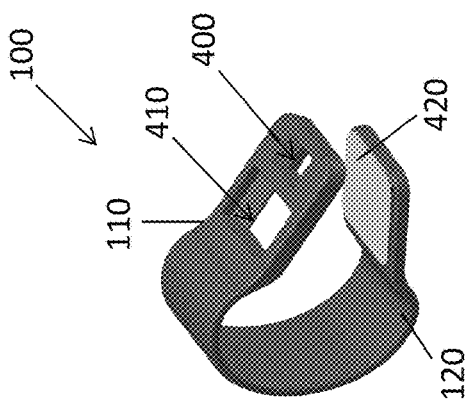
Figure 4C:
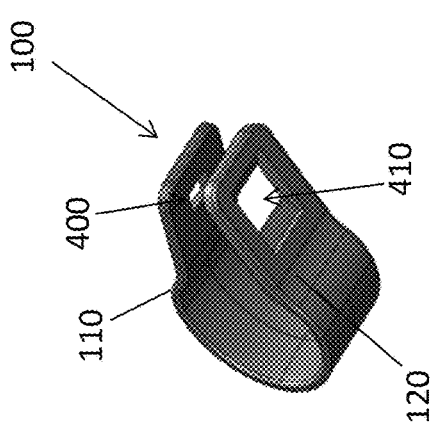
Figure 4D:
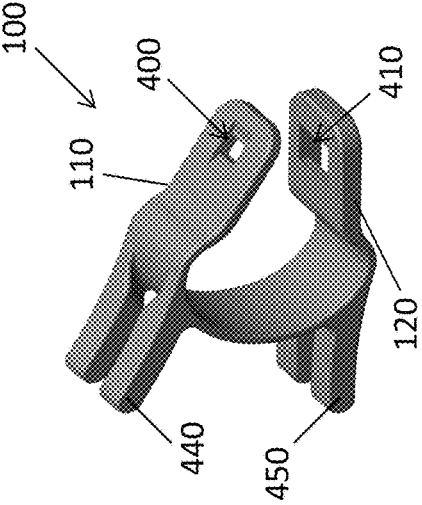
Figure 4E:
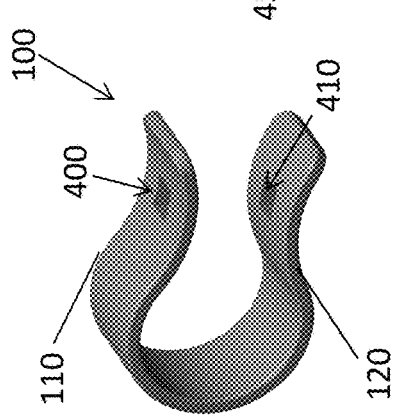
Figure 4F:
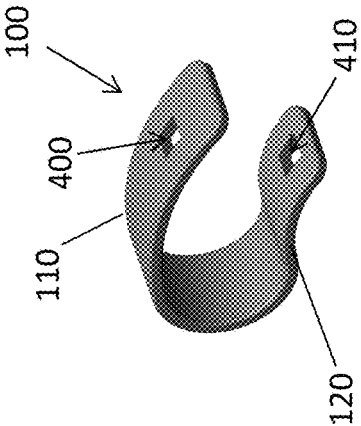

According to some embodiments of the present invention, the PPG sensor is configured to secure to the nasal alar region of the nose, which may also be referred to herein as the "nasal alar", "alar" or "ala", and may also be referred to elsewhere as the nasal "wing". FIG. 3 is an illustration of the structure of the nose in which the nasal alar region of the nose is highlighted. By definition, the ala of the nose is the lateral surface of the external nose, cartilaginous in makeup, which flares out to form a rounded eminence around the nostril. As used herein, the external nasal alar region includes the lateral cartilage region, the lesser alar cartilage region, the greater alar cartilage region, the accessory alar (sesamoid) cartilage region and the alar fibrofatty tissue region. Also included in the definition of the nasal alar region is the alar groove (also referred to as "alar crease"), which is the crescent shaped border of the lateral aspect of the ala, and which includes the alar-facial groove and alar-nasal groove. Thus, the nasal alar sensors referred to herein may be secured onto or over the alar fibro-fatty tissue and/or on or above the alar groove. As used herein, the internal nasal alar region includes the areas of the lateral nasal wall in the nasal alar region, as defined above, but on the inside of the nostril. Particular internal nasal alar locations include the vestibule and the limen of the lateral nasal wall.

In some embodiments of the present invention, the nasal alar PPG sensor includes a clip body that is configured to secure to a nasal alar region of a subject. The discussion of clip body configurations and materials discussed for PPG sensors generally is also applicable to clip bodies for the nasal alar specifically. In some embodiments, the clip body will include a first end portion and a second end portion, whereby the first end portion is configured to secure externally to the nasal alar region and the second end portion is configured to secure internally to the nasal alar region. The first and second end portion may be configured to secure to the same nasal alar site, with the first end portion secured at a particular position externally and the second end portion secured internally directly across the tissue from the first end portion. However, in some embodiments, the first end portion and the second end portion may be configured to secure at different nasal alar positions, such that the second end portion may not sit directly across the tissue from the first end portion, but may be positioned above, below and/or otherwise offset from the first end portion.

Such clip bodies may also include apertures that are sufficiently large or specifically shaped to accommodate different configurations of the emitter and the detector. For example, in some embodiments, two or more emitters may be within or adjacent to the same aperture. In some embodiments, the emitter and detector may be within or adjacent to the same aperture in the clip body. Furthermore, in particular embodiments, the emitter may emit light at an angle that requires a larger aperture or an aperture having a specific shape. The clip body may also have apertures in an array configured to provide monitoring at two or more locations in the nasal alar region.

The clip body may also be shaped to facilitate securing of the clip body, to improve or optimize the quality of the PPG signal, to provide additional comfort to the wearer, to disperse the pressure of the sensor, and/or to facilitate correct placement of the sensor. For example, the clip body may have a convex surface, for example, to follow the contour of the alar fibro-fatty tissue. This contour may allow for more intimate contact of the sensor to the skin, which in turn may facilitate the securing of the clip body and improve the quality of the PPG signal. This concave surface may also guide medical personnel to correctly position the sensor on the fibrofatty tissue. In some embodiments, an end portion may be wider or have a greater surface contact area at a particular point, for example, to disperse the pressure of the clip on the tissue, which may increase the comfort to the subject.

FIG. 4 shows examples of different clip body types that may be useful for securing the sensor to the nasal alar region. FIG. 4A shows a curved or substantially "U-shaped" clip body 100 having a first end portion 110 that has a first aperture 400, and a second end portion 120 that has a second aperture 410. In this embodiment, the first aperture 400 is smaller than the second aperture 410, and this configuration may be appropriate for when an emitter (not shown) is within or adjacent to the first aperture 400, and the detector (not shown) is within or adjacent to the second aperture 410. In this embodiment, the two end portions are not parallel at the point of attachment, but instead are inflected slightly inward. FIG. 4B shows a clip body 100 that may be useful in a reflectance PPG sensor. In this case, the first aperture 400 and the second aperture 410 are both defined within the first end portion 110 of the clip body 100. This may allow for an emitter from the flex circuit to be placed within or adjacent to the first aperture 400 and a detector 410 to be placed within or adjacent to the second aperture 410. The sensor shown in FIG. 4B also includes a reflective surface 420, but in some cases, this reflective surface 420 is not necessary. FIG. 4C shows a clip body that is similar to that shown in FIG. 4A, but the first end portion 110 includes two apertures. Thus, a first emitter may be placed within or adjacent to the first aperture 400 and a second emitter may be placed within or adjacent to an additional aperture 430 in the first end portion 110. The detector may then be placed in the aperture 410 in the second end portion 120 of the clip body 100. The clip bodies shown in FIGS. 4D and 4E are similar to the clip body in FIG. 4A, except that the clip bodies have different curvatures and the second aperture is somewhat smaller. FIG. 4F shows a clip body that is similar to that shown in FIG. 4A, but it includes a first gripping member 440 on a surface of the first end portion 110 and a second gripping member 450 on a surface of the second end portion 120. When the first gripping member 440 and the second gripping member 450 are pressed together, the first end portion 110 and the second end portion 120 of the clip body 100 may separate, thus facilitating the placement of the sensor on a subject. The length of each end portion of the clip body may be varied according to the particular nasal alar region that is to be monitored and, in some cases, according to the size and age of the subject to be monitored.

Figure 5A:
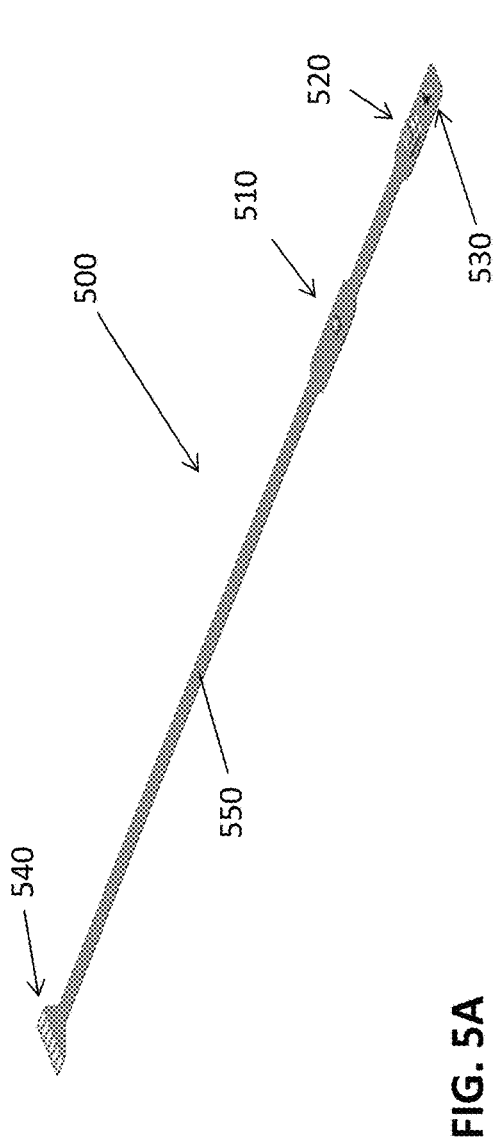
FIG. 5A depicts a flex circuit according to an embodiment of the invention prior to preparation for joining with a clip body.
Figure 5B:
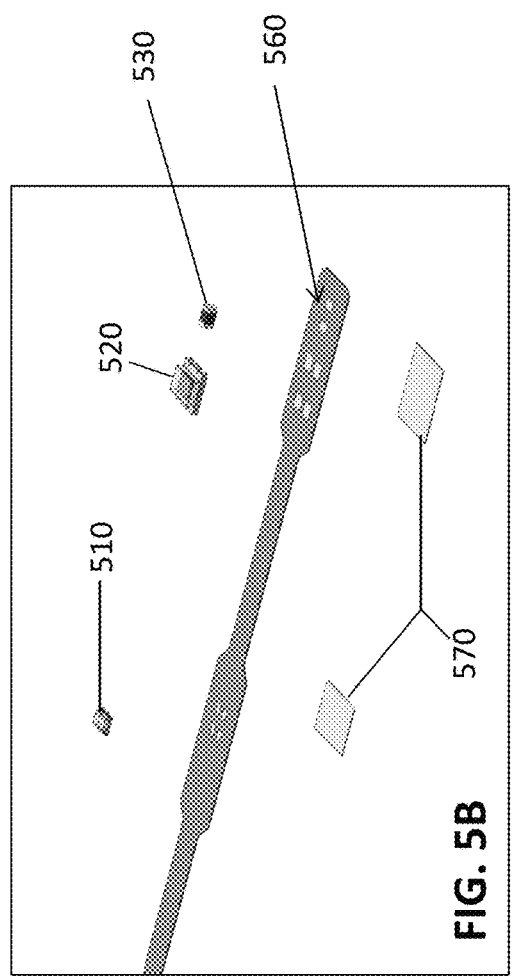
FIG. 5B is a close-up view of a flex circuit prior to the mounting of the electronic components.

The nasal alar PPG sensors may include any suitable flex circuit, including those described above with respect to PPG sensors generally. The flex circuit is typically sized and shaped to facilitate joining with the clip body, and so that at least a portion of the flex circuit may fit within the elastomeric sleeve along with the clip body. However, this may be achieved by a number of different configurations. Referring to FIGS. 5A and 5B, in some embodiments, the flex circuit 500 includes an emitter 510 and a detector 520 that are spaced sufficiently apart so that the emitter 510 can be set within or adjacent to an aperture in the first end portion of the clip body (not shown), and the detector 520 can be set within or adjacent to an aperture in the second end portion of the clip body when the flex circuit is joined with the clip body. In the embodiment shown in FIG. 5A, a secondary respiration detector 530, such as a thermistor, is also mounted on the flex circuit 500. In this case, the secondary respiration detector 530 is near the detector 520, but in other embodiments, the secondary respiration detector 530 may be placed near the emitter 510. The secondary respiration detector 530 may be on any suitable portion of the flex circuit 500, or indeed, on any other part of the PPG sensor, including on or in the clip body or elastomeric sleeves (not shown). In this embodiment, each of the electronic components is mounted to the same side of the flex circuit 500. This configuration may have manufacturing advantages, but in some cases, there may be electronic components on both sides of the flex circuit 500.

In the flex circuit shown in FIG. 5A, an extended portion 550 of flex circuit is present, and once assembled, this extended portion 550, can act as a wire or cable that communicates the PPG signals to a computer or other signal processing device. To that end, the flex circuit 500 may also include a connecting portion 540 for attaching with other cables or wires, or connecting directly with a processing device. In other embodiments, this extended portion 550 of the flex circuit 500 and/or the connection portion 540 may not be included because, for example, an electronic component for wireless communication is included on the PPG sensor.

Figure 6:
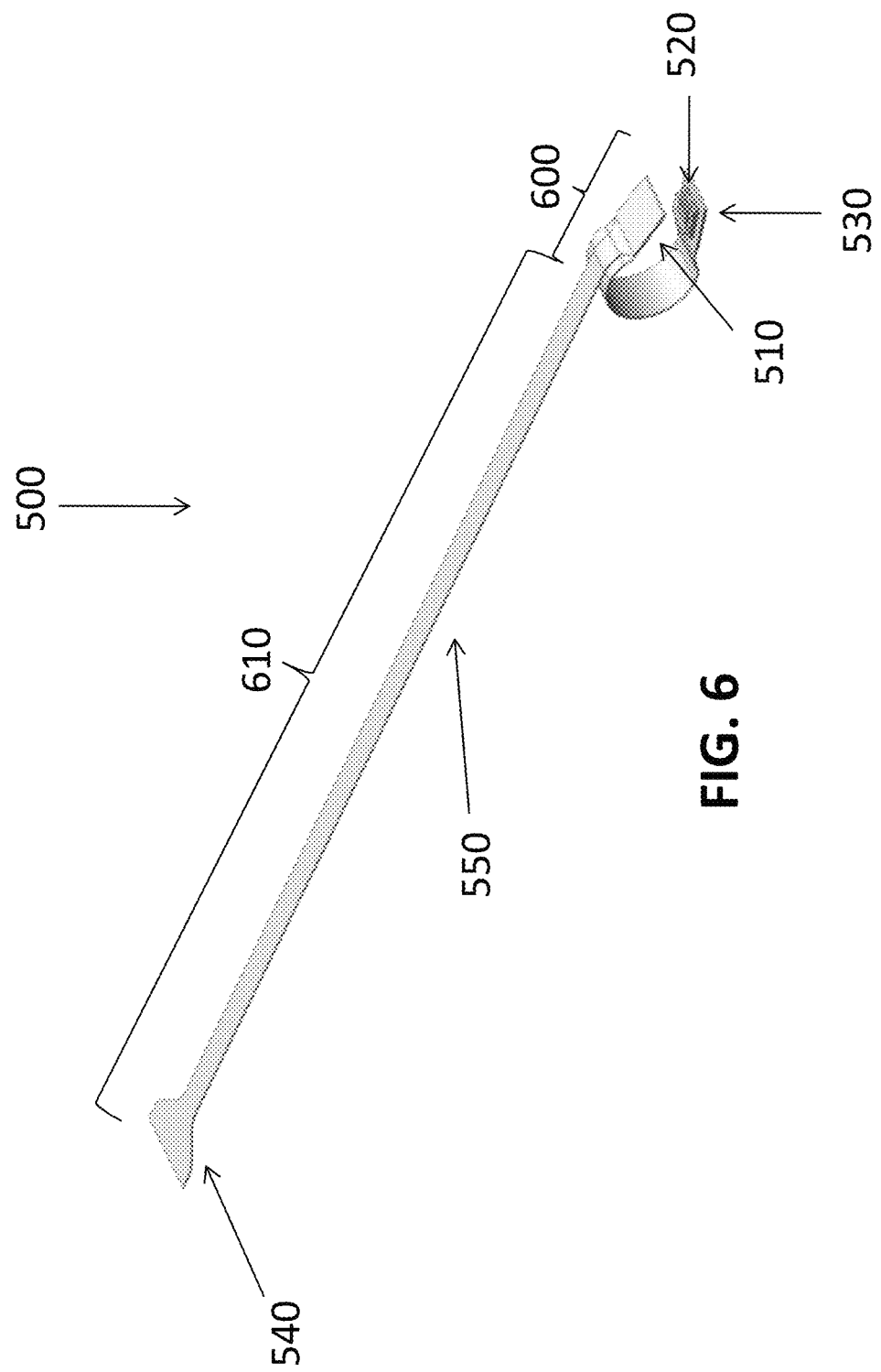
FIG. 6 depicts a flex circuit according to an embodiment of the invention after preparation for joining with a clip body.

FIG. 5B shows the emitter 510, detector 520 and secondary respiration detector 530 prior to soldering onto a pin 560 on the flex circuit 500. FIG. 5B also shows two pieces of double sided tape 570, which are used to adhere the flex circuit into a folded position. FIG. 6 shows the flex circuit shown in FIG. 5B after modification by folding and adhering certain sections with the double-sided tape. In this case, the portion of the flex circuit 500 that includes that detector 520 and the secondary respiration detector 530 was folded/adhered, so that the detector 520 and secondary respiration detector 530 are on opposite faces of the flex circuit. This may allow for the detector 520, once joined with the clip body, to be positioned facing the tissue and thus able to detect light from the emitter 510, while allowing the secondary respiration detector 530 to access airflow in or near the nasal cavity. In FIG. 6, the flex circuit 500 was also folded/adhered to create a sensor portion 600 of the flex circuit and a cable/connector portion 610 of the flex circuit.

Any suitable type of elastomeric sleeve may be used with the nasal alar PPG sensors, including those described above with reference to PPG sensors generally. In some cases, the elastomeric sleeve may be configured in the same shape as the portion of the clip body that is to be inserted therein, but in other cases, the sleeve may longer or wider than the clip body, and the external surfaces of the elastomeric sleeve may be flat or contoured. In some embodiments, the elastomeric sleeve may be manufactured so that a surface of the elastomeric sleeve generally follows a contour of a particular surface of the nose in the nasal alar region. In such embodiments, the contour may provide for a desirable contact between the sensor and the skin, which may improve signal strength and/or quality and may, in some cases, improve attachment or affixation of the sensor to the nasal alar. A contoured nasal alar PPG sensor may also provide an intuitive guide for placement, which may be helpful for medical personnel to ensure proper placement of the sensor.

In particular embodiments, the elastomeric sleeve is configured to minimize pressure on a tissue surface. Thus, in some cases, the clip body is configured so that the pressure on the internal and external tissue between the first end portion and the second end portion of the nasal alar probe is less than 100 mm Hg, less than 80 mm Hg, less than 50 mm Hg, less than 30 mm Hg, or less than 15 mm Hg. In some embodiments, the pressure on the internal and external tissue between the first end portion and the second end portion of the nasal alar probe is in a range of 10 mm Hg and 100 mm Hg, in some embodiments, in a range of 15 mm and 50 mm Hg, and in particular embodiments, in a range of 15 mm and 30 mm Hg.

The elastomeric sleeve may also have apertures or gradations in thickness, for example, to facilitate the operation of the electronic components mounted on the flex circuit. In some embodiments, the surface of the elastomeric sleeve may be thinner in the portion of the sleeve that light is emitted through to increase light efficiency. However, if the sleeves are made from suitably transparent material, or include a transparent window, this may not be necessary or desirable. As another example, the elastomeric sleeve may have an aperture in the sleeve so that a secondary respiration detector on the flex circuit may be exposed to air flow in or near the nasal cavity. This may also not be necessary however, and the secondary respiration detector may be included on a part of the flex circuit that is not enveloped by an elastomeric sleeve. As with the apertures of the clip body, the shape and number of apertures in the elastomeric sleeves may vary according to the needs and designs of a particular alar sensor.

In some embodiments, the nasal alar sensor includes two or more elastomeric sleeves. In particular embodiments, nasal alar PPG sensors include a first elastomeric sleeve that envelopes a first end portion of the clip body and the flex circuit attached or adjacent thereto, and a second elastomeric sleeve that envelops a second end portion of the clip body and the flex circuit that is attached or adjacent thereto. FIGS. 7A and 7B provide two views of a pair of elastomeric sleeves 700 that may be used in a nasal alar sensor according to an embodiment of the invention. In this case, a first elastomeric sleeve 710 includes a fitted portion 720 and a cushion portion 730. The fitted portion 720 is shaped to be approximately the same shape as the clip body that is to be inserted therein. The cushion portion 730, however, extends wider than the fitted portion 720, and in this case, is rectangular and somewhat concave. A second elastomeric sleeve 740 also includes a fitted portion 750 and a cushion portion 760, but in this case, the cushion portion 760 of the second elastomeric sleeve 740 is smaller than the cushion portion 730 of the first elastomeric sleeve 710, has a rounded shape and is somewhat convex. As shown in FIGS. 7A and 7B, the pair of elastomeric sleeves 700 may be configured so that cushion portion 730 of the first elastomeric sleeve 710 and the cushion portion 760 of the second elastomeric sleeve 740 are suitably matched to promote secure attachment and intimate contact of the alar tissue between the surface of the elastomeric sleeves. For example, in this case, an alar tissue may be secured between the convex cushion portion 760 of the second elastomeric sleeve 740 and the concave cushion portion 730 of the first elastomeric sleeve 710.

Referring to FIG. 7C, in some embodiments of the invention, the pair of elastomeric sleeves 700 does not include a separate fitted portion and cushion portion, but each elastomeric sleeve is sized and shaped is the same general shape as the clip body 100 it is envelops. In other embodiments, the first elastomeric sleeve 710 and the second elastomeric sleeve 740 may be of uniform shape, as shown in FIG. 7C, but may extend wider and/or longer than the end portions of the clip body 100.

Figure 8:
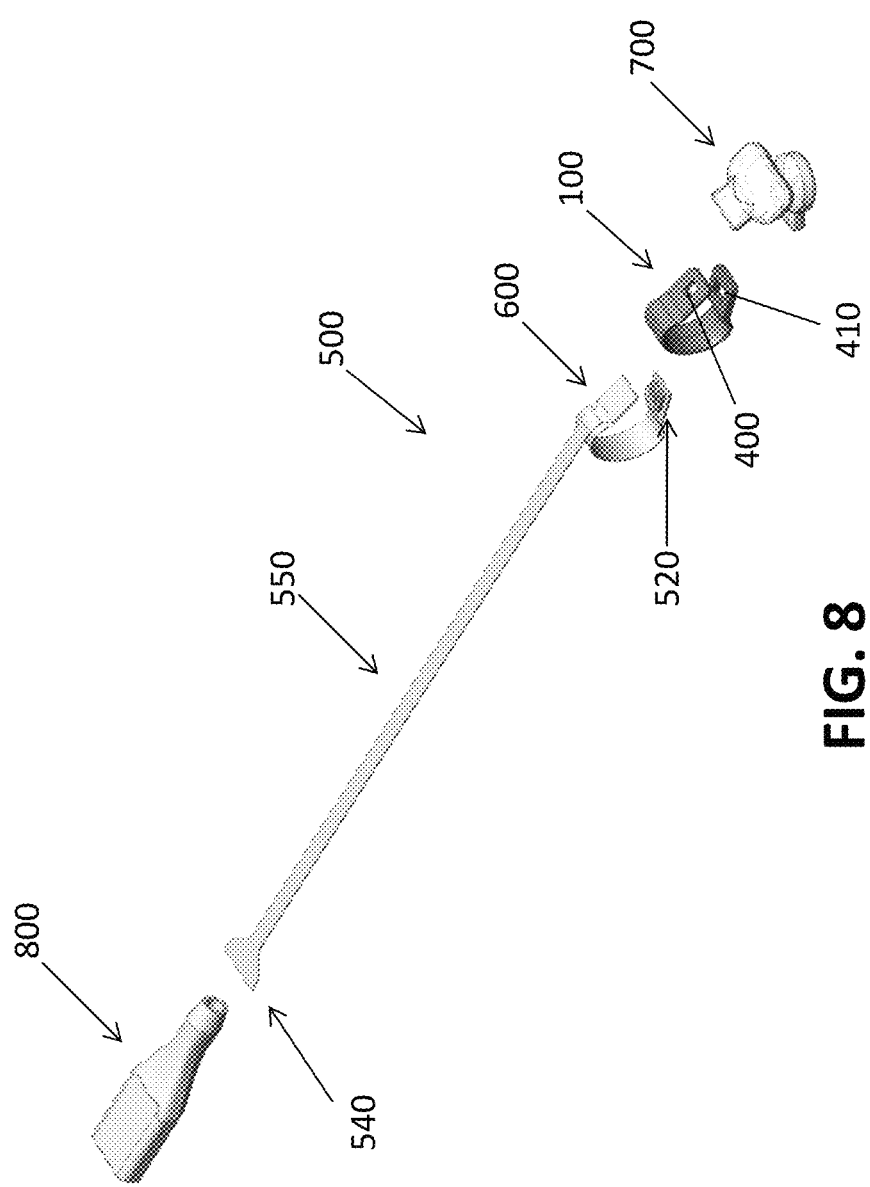
FIG. 8 is an illustration of a clip body, flex circuit and a pair of elastomeric sleeves prior to assembling the clip body, flex circuit and elastomeric sleeves to form a nasal alar sensor according to an embodiment of the invention.

The clip body and the flex circuit may be joined in any suitable manner, and enveloped into the elastomeric sleeve in any suitable manner. However, FIGS. 8-14 illustrate how, in particular embodiments, the clip body 100, flex circuit 500, and the pair of elastomeric sleeves 700 can combine to form a nasal alar PPG sensor according to an embodiment of the invention. FIG. 8 shows an expanded view of how the clip body 100, flex circuit 500 and pair of elastomeric sleeves 700 might be configured so that they can be joined and bound together. It can be seen that the sensor portion 600 of the flex circuit 500 is of the appropriate length to wrap around the clip body 100, and the emitter (not shown) and the detector 520 may be positioned on the flex circuit to fit within a first aperture 400 and second aperture 410 in the clip body 100, respectively. The pair of elastomeric sleeves 700 are shaped, and the internal size of the sleeve configured, to envelop the clip body 100 and the flex circuit 500 attached or adjacent thereto. The sensor thus configured has the extended portion 550 of the flex circuit 500 acting as a wire or cable, and an adapter 800 may be coupled with the connecting portion 540 of the flex circuit 500.

FIG. 9 shows the same flex circuit 500, clip body 100 and pair of elastomeric sleeves 700 from below. From this angle, it can be seen that the flex circuit 500 is configured to provide a secondary respiration detector 530 on the underside of the clip body 100, and that the bottom elastomeric sleeve has an aperture 900 that allows the secondary respiration detector 530 to be exposed to air flow from the nasal cavity. FIG. 10 shows the same flex circuit 500, clip body 100 and pair of elastomeric sleeves 700. From this perspective, the emitter 510, detector 520 and secondary respiration detector 530 can be each be identified.

Figure 11A:
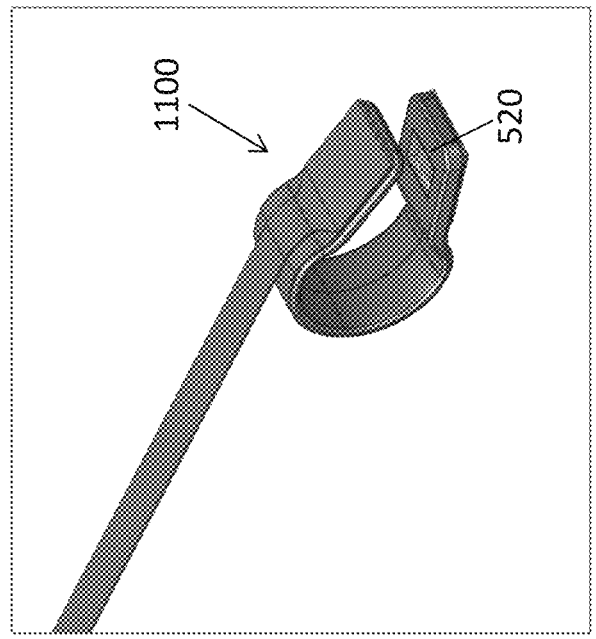
FIG. 11A shows a clip body and flex circuit prior to joining.
Figure 11B:
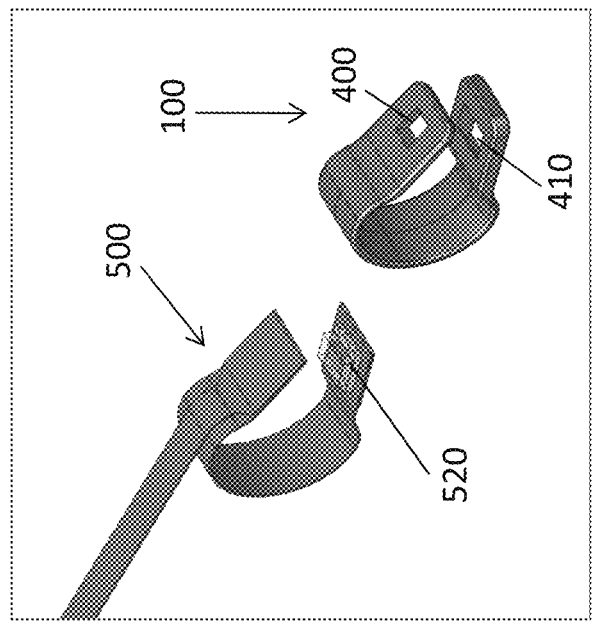
FIG. 11B shows the same clip body and flex circuit after joining.

FIGS. 11A and 11B illustrate the joining of the flex circuit with the clip body. Specifically, the flex circuit is wrapped around the clip body, the emitter (not shown) is set within the first aperture 400 in the clip body 100 and the detector 520 is set within the second aperture 410 in the clip body 100 to form a joined flex circuit/clip body 1100. Thus joined, the clip body 100 and the flex circuit 500 attached or adjacent thereto are ready to be inserted into the elastomeric sleeves (not shown). As described elsewhere herein, in some embodiments, electronic components such as the emitter 510 and detector 520, may not be set within an aperture, and many other configurations are possible (see, e.g., FIG. 2A-2F).

Figure 12A:
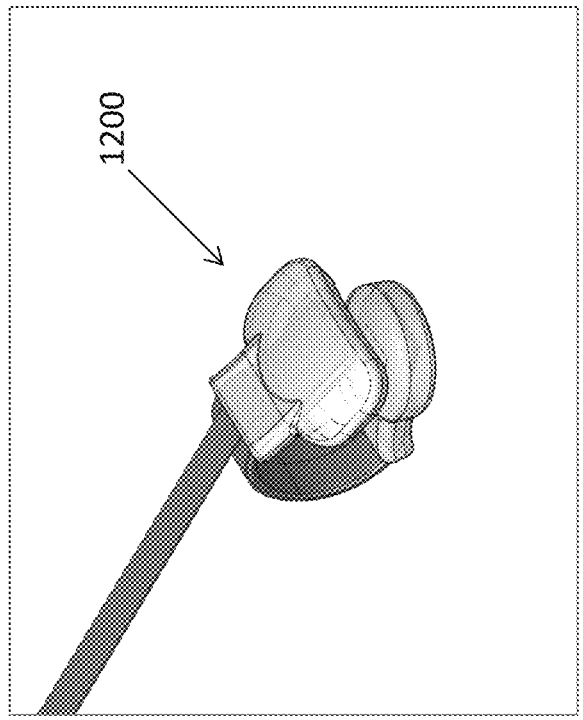
FIG. 12A shows a joined clip body/flex circuit and a pair of elastomeric sleeves prior to inserting the joined clip body/flex circuit into the elastomeric sleeves.
Figure 12B:
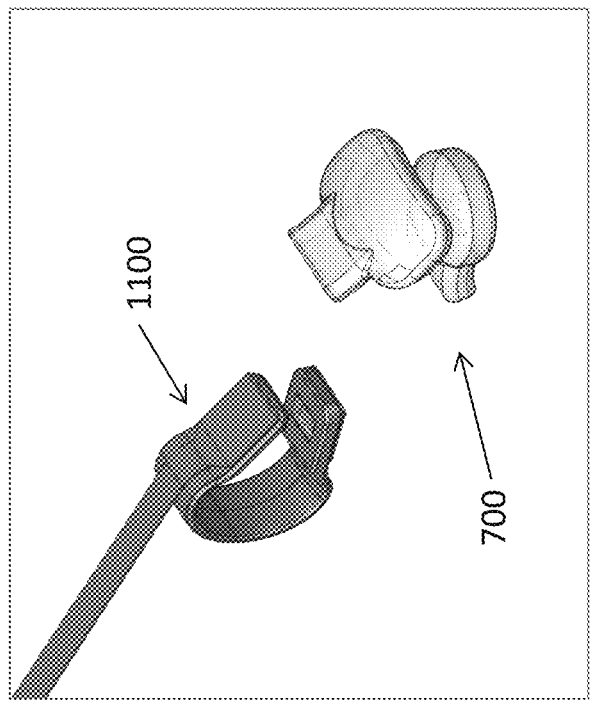
FIG. 12B shows the alar sensor, wherein the joined clip body/flex circuit has been inserted into the elastomeric sleeves.

Referring to FIGS. 12A and 12B, the joined flex circuit/ clip body 1100 may then be inserted into the pair of elastomeric sleeves 700 to form a nasal alar sensor 1200. As described elsewhere herein, in some cases, the joined flex circuit/clip body 1100 and/or the inside of the elastomeric sleeves 700 may be lubricated prior to insertion. Additionally, as described with respect to PPG sensors generally, in some embodiments, a swelling agent may also be applied to the elastomeric sleeves 700 and/or the joined flex circuit/clip body 1100 to facilitate the binding of the flex circuit and clip body within the elastomeric sleeves 700.

Figure 13:
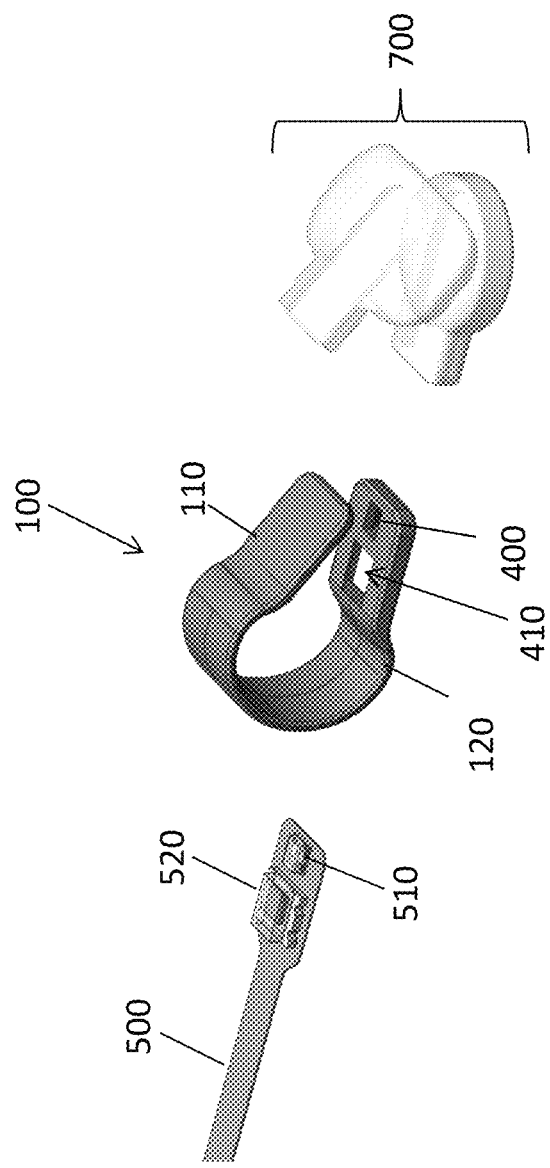
FIG. 13 shows a flex circuit, clip body and pair of elastomeric sleeves that may be useful to form a reflectance PPG nasal alar sensor according to an embodiment of the invention.

FIG. 13 provides an illustration of a flex circuit 500, clip body 100 and pair of elastomeric sleeves 700 that may be joined to form a reflectance PPG sensor. In this case, the emitter 510 and the detector 520 are mounted next to each other on the flex circuit 500, and the first aperture 400 and the second aperture 410 are both defined within the second end portion 120 of the clip body 100. Thus, when the flex circuit wraps around the clip body 100, the emitter may fit within the first aperture 400 and the detector 520 may fit within the second aperture 410. The joined flex circuit/clip body (not shown) may then be inserted into the pair of elastomeric sleeves 700.

Figure 14A:
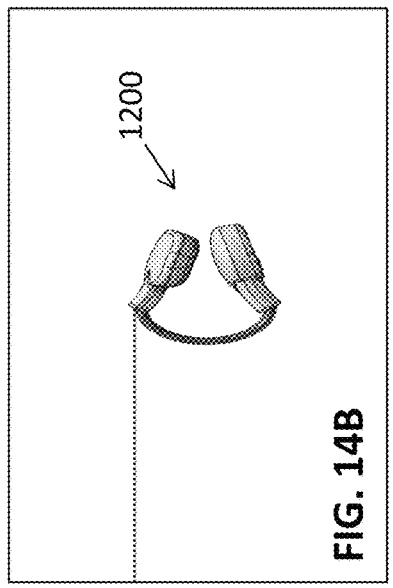
FIGS. 14A-14C show alternate views of a nasal alar sensor according to an embodiment of the invention.
Figure 14B:
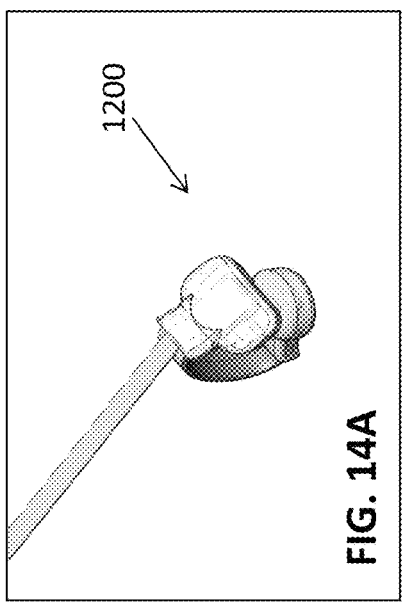
Figure 14C:
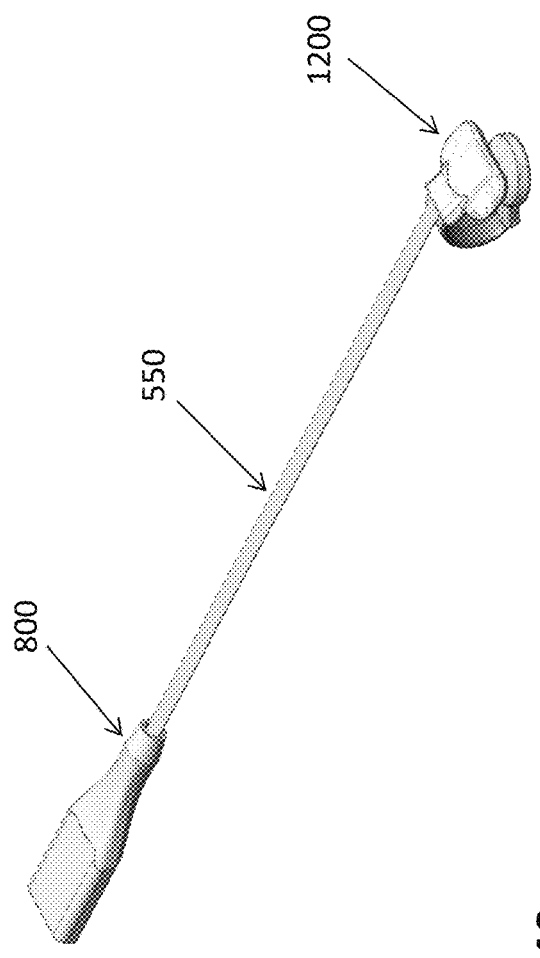
Figure 15:
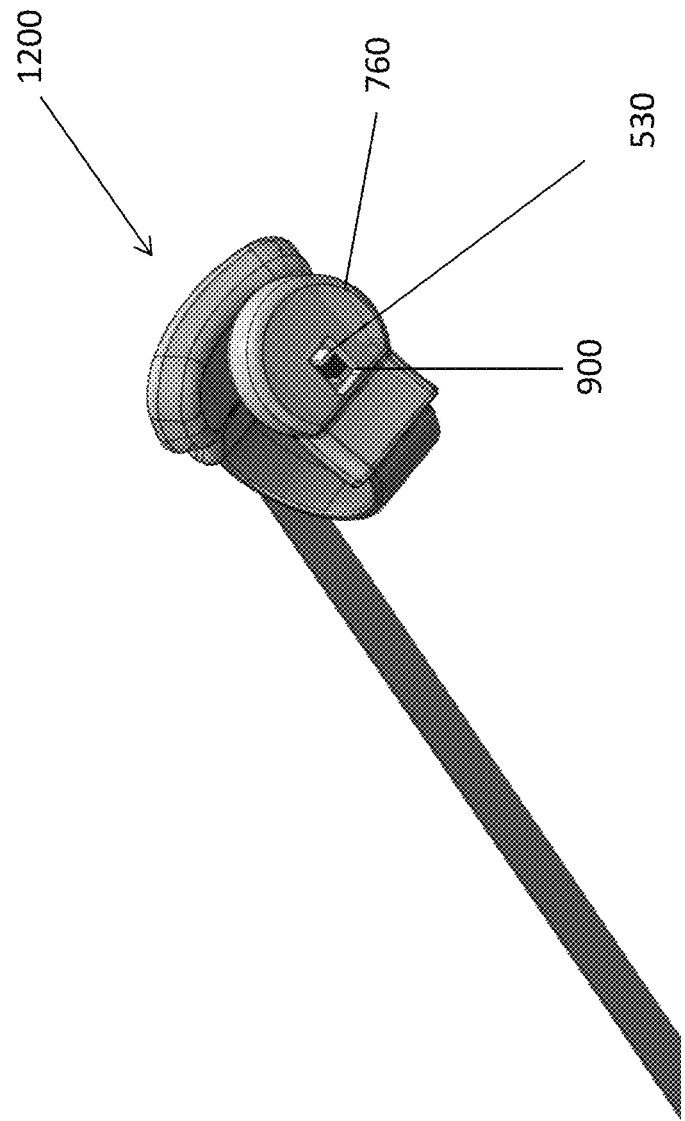
FIG. 15 shows a secondary respiration detector on the bottom of an end portion of an alar sensor according to an embodiment of the invention.

FIGS. 14A and 14B show two different views of the nasal alar sensor 1200 according to the embodiments of the invention. FIG. 14A is a view looking down on the top of a nasal alar sensor 1200, and 14B is a side-view of the nasal alar sensor 1200. FIG. 14C shows the nasal alar sensor 1200 with the extended portion of the flex circuit 550 and the connector portion (not shown) coupled with the adaptor 800. FIG. 15 shows the underside of the nasal alar sensor 1200, and shows that a secondary respiration detector 530 may fit through the aperture 900 in the second elastomeric sleeve 760 so that it is exposed to the nasal airflow.

The size and shape of the nasal alar sensor may vary. In some embodiments, a single size and shape of alar sensor may be used on all patients. However, in other embodiments, the sensor may be manufactured at different sizes and configurations to accommodate different types of patients, including children, young adults and adults, and to accommodate different nose sizes and shapes. The size and shape of the alar sensor may also vary to secure to different portions of the alar region. This may affect the distance the sensor is inserted into the nostril. In some cases, the intranasal portion of the sensor extends into the nostril a distance in a range of about 0.5 to about 2.5 cm, and in some embodiments, at a distance less than 1 cm. In some embodiments of the invention, the nasal alar sensor may be agnostic with respect to which nostril it is applied to, which may simplify the placement process for medical personnel, and may also allow for alternating the nostril which is monitored.

The nasal alar sensors, according to particular embodiments, may also include a nasal cannula for delivery of breathing gases, such as oxygen or oxygen-enriched air. The nasal cannula may be incorporated into the alar sensor in a number of different ways. For example, in some embodiments, the nasal cannula may be affixed to the outside (or inside) of the sensor so that it is inserted into the nostril with the end portion of the sensor that secures inside the nasal cavity. As another example, in some cases, the clip body may have an aperture defined therein, so that the cannula may run through the clip body. In such case, the elastomeric sleeves may have an opening that allows the cannula to enter or exit the sensor. As an additional example, the cannula may run between clip body and flex circuit, and such a cannula may also enter and exit the sensor through openings in the elastomeric sleeves.

Accessories for Use with Nasal Alar Sensors

Figure 16:
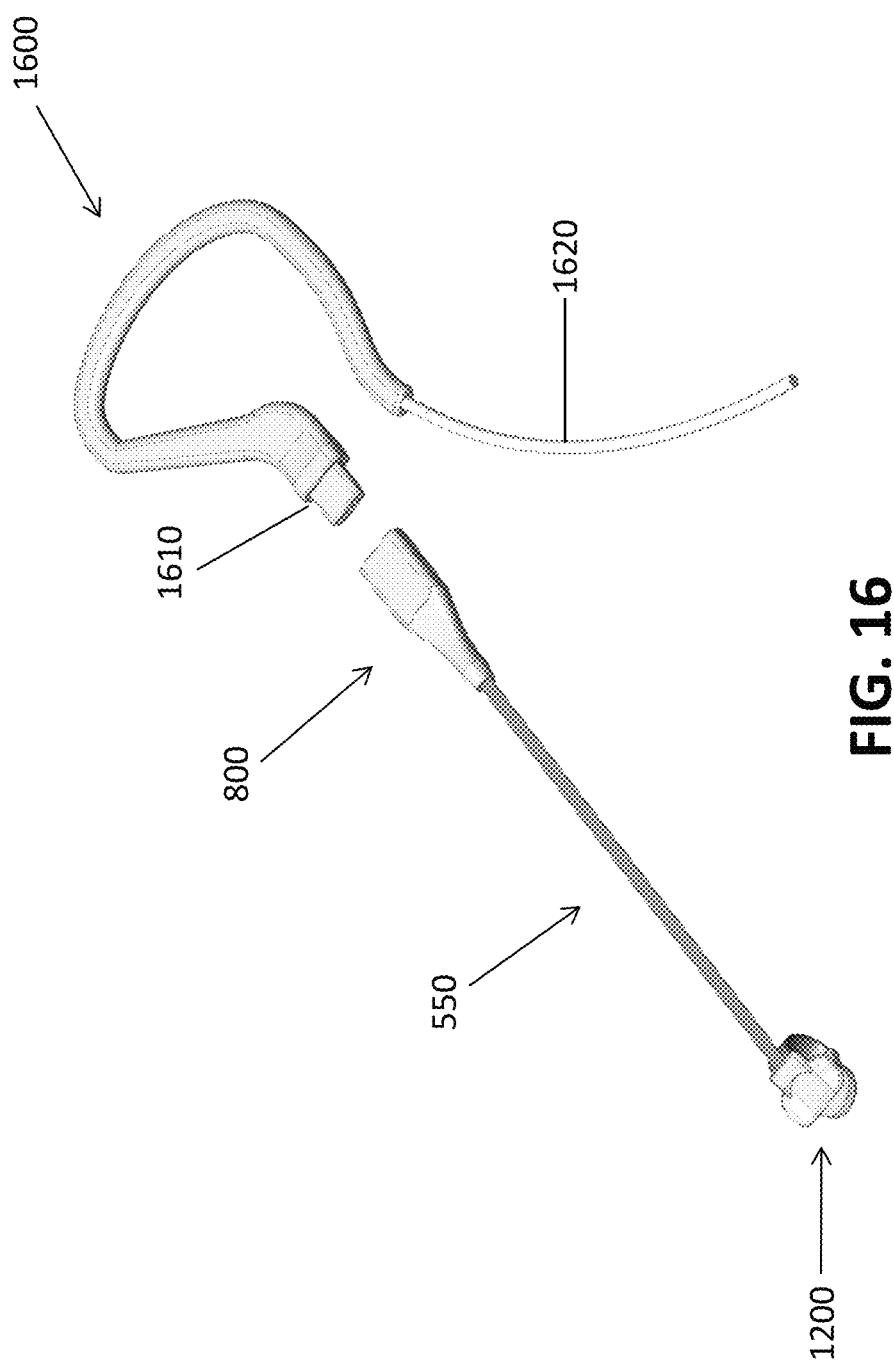
FIG. 16 shows an alar sensor with a connector and an earpiece configured to interface with the sensor.

Further provided according to some embodiments of the present invention are earpieces that are configured to direct the flex circuit and/or other cables behind the patient's ear and so lead them away from the patient's face. The earpiece may also be configured to couple with the flex circuit, connector portion or adaptor instead of merely guide the wires or cables behind the patient's ear. In some cases, the flex circuit may be configured to directly couple with the earpiece, with or without an adaptor, and in some cases, additional wires and connectors may be included between the flex circuit and the earpiece. As the primary purpose of the earpiece is to guide the cabling away from the patient's face, a number of different styles of earpieces may be suitable. FIG. 16 shows an example of one particular earpiece 1600. In this case, the nasal alar sensor 1200 is connected to an extended portion 550 of the flex circuit 500, and the connector (not shown) fitted with an adapter 800. This adaptor 800 interfaces with the earpiece connector 1610, and the signal is transmitted through wires or cables running through or with the earpiece 1600. A wire or cabling 1620 then runs from the earpiece 1600 to additional connectors, wires, cables and/or processing devices.

Also provided according to embodiments of the present invention are applicators that may be used to place a clip body sensor onto a tissue. Such applicators may be facilitate and expedite the placement of the sensor on a subject, and so may be particularly useful for medical personnel. The applicator may separate the two end portions of the sensor, thereby allowing the sensor to slide over a tissue, such as the alar fibrofatty tissue and/or the lateral nasal sidewall. In some embodiments of the invention, the PPG sensor is initially attached or joined with the applicator, and the applicator is then detached after the sensor is secured, but in other embodiments, the sensor applicator is a separate device that is joined with the sensor by the medical personnel.

In some embodiments of the invention, the device applicator may operate in a "clothespin" type fashion. For example, in some embodiments, devices for placing a sensor on a patient may include a device body having two arms. The first device arm may be configured to attach or be adjacent to a first end portion of the clip body of the nasal alar probe during application, and the second device arm may be configured to attach or be adjacent to the second end portion of the clip body during application. In some embodiments, the device is configured such that both the first device arm and the second device arm are placed between the first end portion and the second end portion of the clip body of the sensor. In other embodiments, the first device arm may attach to the first end portion of the clip body of the sensor, and the second device arm may attach to the second end portion of the clip body of the sensor.

The device arms may then be attached to two handles or grips, such that when the two handles or grips are pressed together, the first device arm and second device arm separate. This may use a lever mechanism, such as a first class double lever mechanism. When the two device arms separate from each other, the first end portion and the second end portion of the clip body may also separate from one another by virtue of being attached to the device arms, or by virtue of the device arms being between the end portions. The device may also include a "living hinge", which separates the device arms from the handle portion of the sensor, and in some cases, the device is a single molded plastic piece. In some cases, the living hinge may spring back to its original configuration after placement of the nasal alar sensor.

Figure 17:
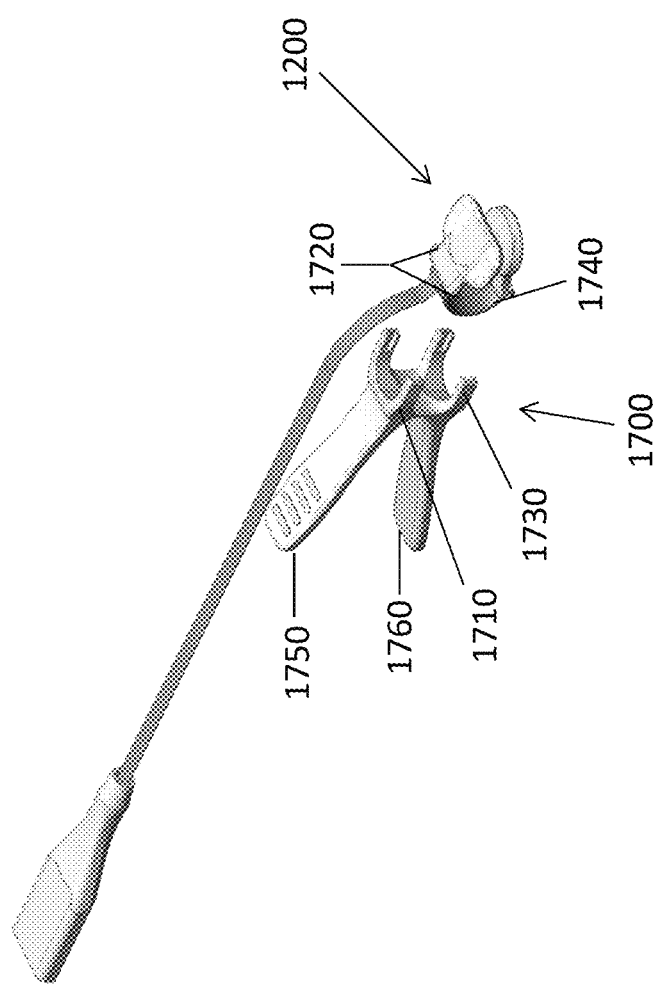
FIG. 17 shows a nasal alar sensor and a sensor applicator according to an embodiment of the invention.
Figure 18:
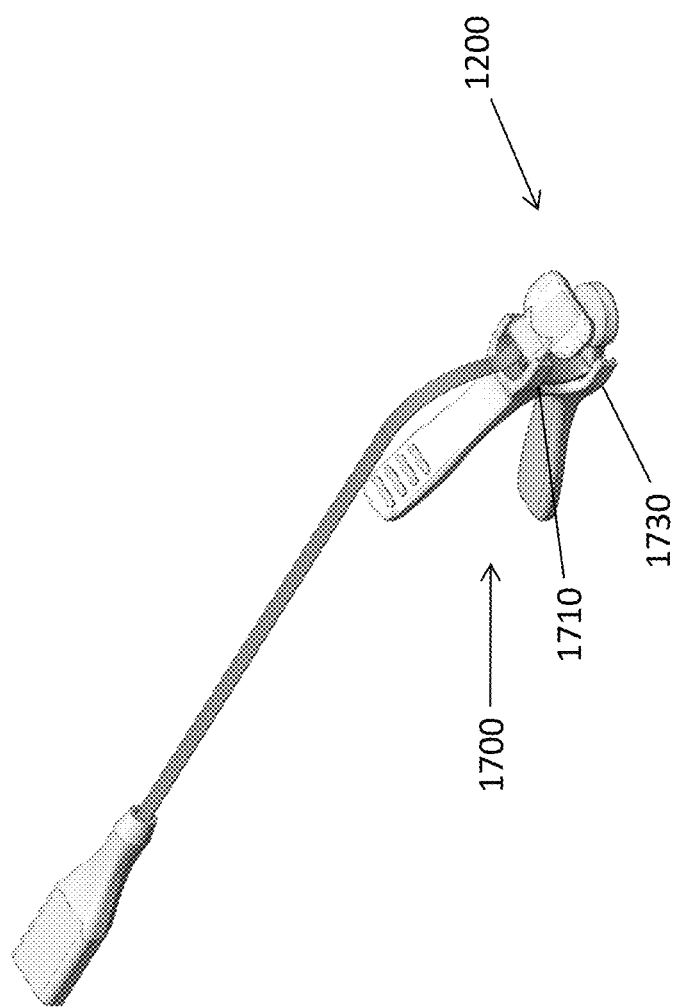
FIG. 18 shows the nasal alar sensor and sensor applicator from FIG. 17 after attachment.
Figures 19A, 19B:
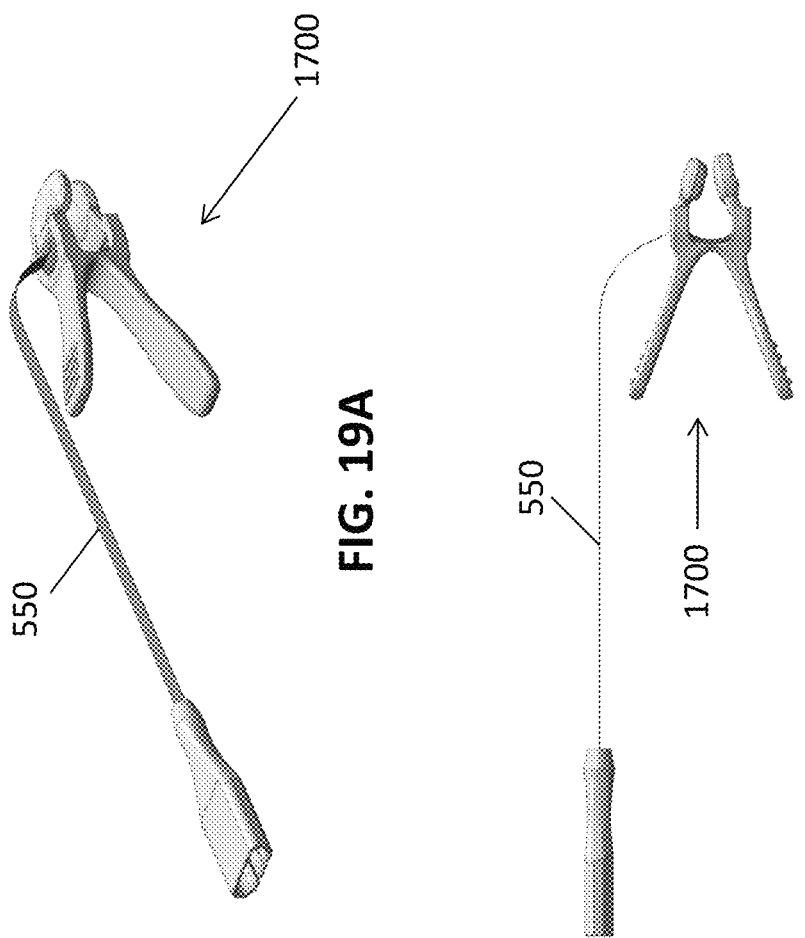
FIGS. 19A and 19B show alternate views of the attached nasal alar sensor and applicator from FIG. 18.

Referring to FIG. 17, in some embodiments, the applicator 1700 is configured such that the first device arm 1710 attaches to at least one side edge 1720 of the first end portion of the sensor 1200 and the second device arm 1730 attaches to at least one side edge 1740 of the second portion of the sensor 1200. The first device arm 1710 and the second device arm 1730 may be configured to attach to any part of the end portion of the sensor 1200. For example, the first device arm 1710 and/or second device arm 1730 may be configured to attach to at least one side edge 1720 of the elastomeric sleeve, and/or at least one side edge 1720 of the clip body. The first device arm 1710 and the second device arm 1730 may separate when the first handle portion 1750 and the second handle portion 1760 are pressed together. FIG. 18 shows the separation of the end portions of the sensor body 1200 by the applicator 1700. It can be noted that as the first device arm 1710 and the second device arm 1730 separate, so do the end portions of the sensor 1200. Once the sensor is applied, the first device arm 1710 and the second device arm 1730 may slip off of the sensor. FIGS. 19A and 19B show two different views of the applicator attached to the PPG sensor. In this case, the applicator 1700 is configured so that the extended portion of the flex circuit 550, or other cabling, runs over the top of the applicator 1700.

Figure 20:
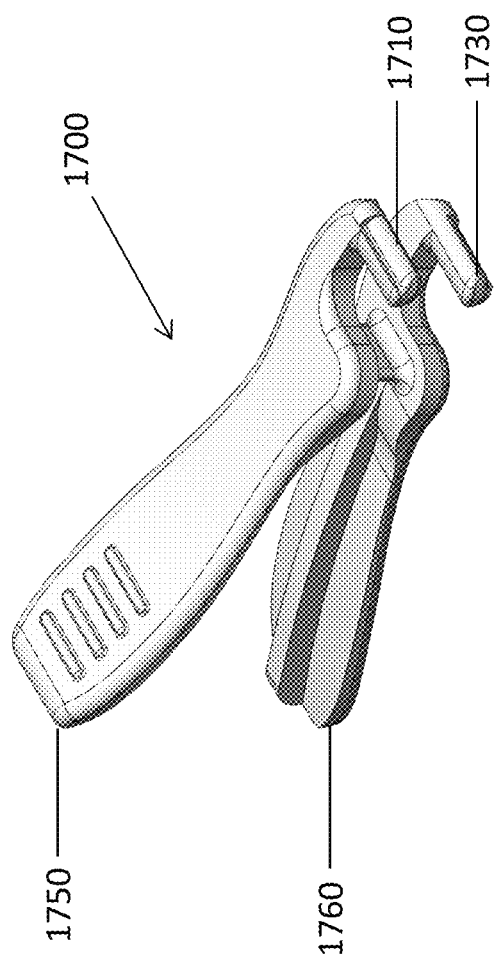
FIG. 20 shows another example of a sensor applicator according to an embodiment of the invention.
Figures 21A, 21B:
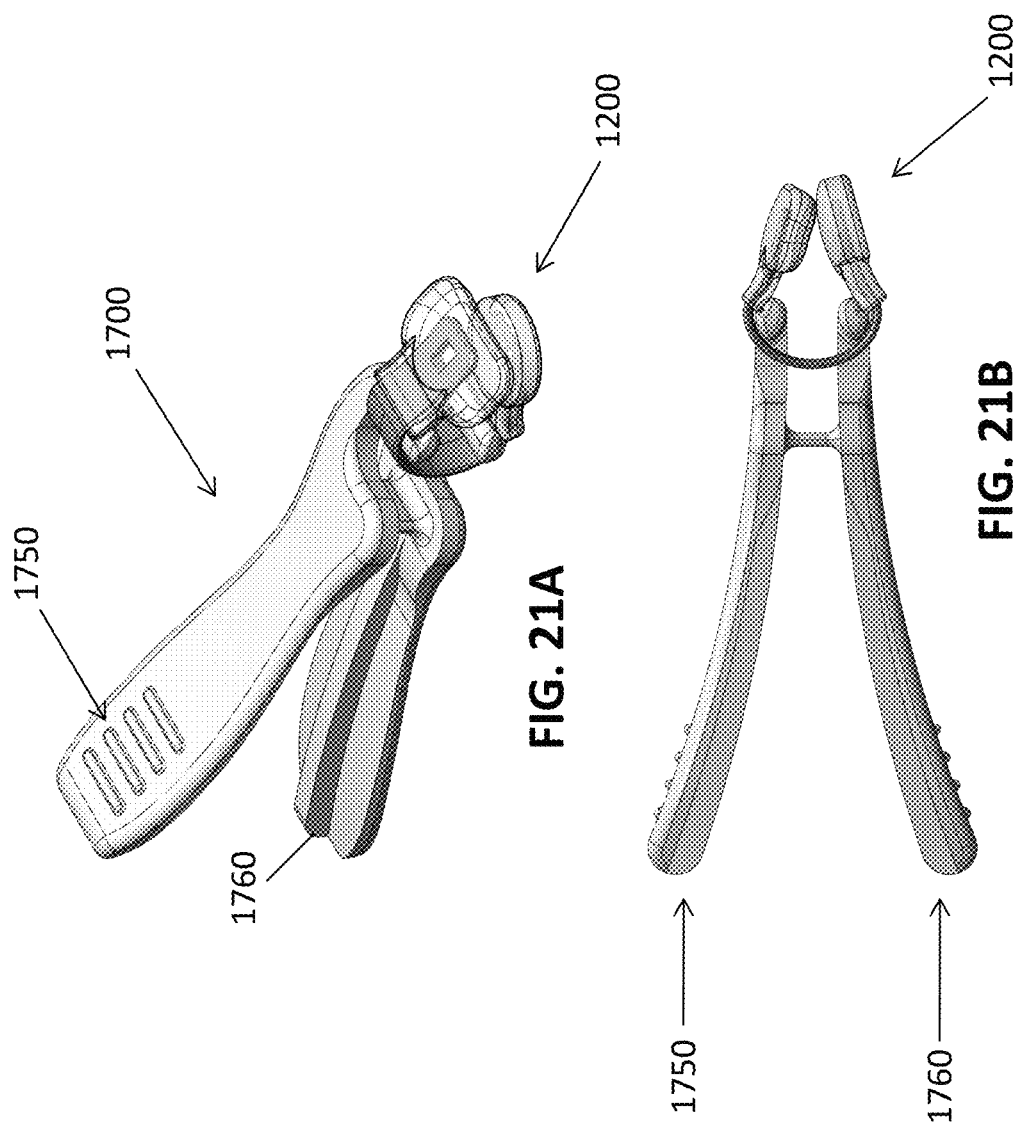
FIGS. 21A and 21B shows alternate views of the sensor applicator of FIG. 20 as joined with a nasal alar sensor.

FIG. 20 illustrates another example of an applicator according to an embodiment of the invention. In this case, the first device arm 1710 and the second device arm 1730 do not attach to the sensor, but instead each cantilever arm is configured to hook between the first and second end portion of the sensor. This device has a living hinge, and when the first handle portion 1750 and the second handle portion 1760 of the applicator 1700 are pressed together, the first device arm 1710 and the second device arm 1730 separate from each other. When the first device arm 1710 and the second device arm 1730 are hooked between the two end portions of the alar sensor, the end portions separate as the device arms separate. Once the device is applied, the hook on each device arm can slide out from between the first end second end portion of the sensor. FIGS. 21A and 21B show the same applicator as hooked into a nasal alar sensor.

While the applicators described herein may be configured to work with nasal alar sensors according to embodiments of the present invention, the applicators described herein may also be configured for use with other sensors that have a clip body. The size and shape of the applicator may vary according to the type of clip body sensor it is to be used with.

Also provided according to embodiments of the invention are sensor kits. Such kits may include a PPG sensor according to an embodiment of the invention, and an applicator configured to secure the sensor to the appropriate tissue site. In particular embodiments, the PPG sensor is a nasal alar sensor and the applicator is configured to work with and place the alar sensor on a subject. In some embodiments, the kit may include other accessories, such as an earloop, tape and/or cleaning products. The kit may also allow for the alar sensor, applicator, and any other accessories, to be contained within sterile packaging. The packaging, once opened, may provide a sterile sensor and applicator, and in some cases, the applicator may already be joined or attached to the sensor so that the sensor can be immediately placed on a patient. Once placed on the patient, the applicator may then be removed. Furthermore, in some embodiments, the sensor and/or applicator may be disposable so that it can be discarded after use.

Systems and Methods For Nasal Alar Sensors

The nasal alar sensors described herein may be used in any suitable fashion, and with any suitable signal processing apparatus or method. Thus, in some embodiments, provided are systems that include at least one nasal alar sensor according to an embodiment of the invention. Such systems may also include a processing apparatus, such as a computer or other analytical equipment, that is communicatingly connected to the nasal alar sensor. Examples of systems and methods that may be used in combination with the nasal alar sensors described herein may be found in U.S. Pat. Nos. 6,909,912, 7,127,278, 7,024,235, 7,785,262, 7,887,502, U.S. Publication No. 2008/0058621, U.S. Publication No. 2008/0190430, U.S. Publication No. 2010/0192952, PCT Application No. PCT/US2011/048083 and PCT/US2011/046943, the contents of each of which are incorporated herein by reference in their entirety.

The nasal alar sensors may be secured to the patient in any suitable manner. For example, once the alar sensor is placed onto a subject, the connector/adapter may be connected to a signal processing apparatus, and signals can be generated. In embodiments wherein a wireless sensor is used, no connection of wires or cables may be necessary for use. In some cases, the sensor may be additionally secured by taping the sensor, flex circuit and/or any additional cabling. As described above, this may ensure that the sensor remains in place despite patient movement or jostling of the sensor or cables, for example, by medical personnel. In some cases, a lubricant may be applied to the nasal alar sensor or the skin/mucosa to which it is to be applied to improve signal and/or to properly situate the sensor. In such cases, taping of the sensor and/or cables may also aid in securing the sensor to the patient.

In general, the end portion of the nasal alar sensor that secures externally to the nasal alar region includes at least one emitter and the end portion that secures internally includes at least one detector. However, in some cases, the emitter(s) may be included in the end portion that secures internally, and the detector(s) may be included in the end portion that secures externally. The advantage of securing the detector internally is that there is less ambient light within the nasal cavity, which may be beneficial for minimizing signal noise. However, in some cases, such as when opaque elastomeric sleeves with transparent windows are used, the ambient light may not significantly affect the signal, and so including the detector(s) externally is acceptable. In reflectance PPG, the emitter(s) and detector(s) are secured to the same face of the tissue. In such cases, the emitter(s) and detector(s) may be secured to the external surface of the nasal alar or may be secured to an internal surface of the nasal alar.

The nasal alar sensor may also be placed on different alar tissues over time. For example, the nasal alar sensor may be placed onto a first lateral nasal sidewall of a first nostril, and then, after a time, it may be removed from the first nostril of the patient, and placed onto the lateral nasal sidewall of the patient's other nostril. While this may often not be necessary, in some cases, such as when the patient needs to wear the sensor for long periods of time, switching or alternating nostrils may provide additional patient comfort.

As described above, nasal alar sensors may be used for determining respiration rate and/or other respiratory parameters and conditions. As such, the nasal alar PPG sensor may be used as a respiration detector. In some embodiments, the nasal alar sensors described herein may be useful with a secondary respiration detector as well, either as part of the sensor or as a separate device, to monitor respiration in a patient. The data from two or more different respiration detectors may be compared, including in real time, which may provide additional information and/or enhanced confidence of the determination of respiratory parameters. As described elsewhere herein, secondary respiration detectors include, but are not limited to, thermistors, thermocouples, RTDs, moisture detectors, capnometers, microphones, pressure sensors, nasal airway flow detectors, such as nasal flow transducers, nasal airway pressure (NAP), and via detectors of vibrations in the ear.

The nasal alar sensors described herein may be used in combination with other physiological monitors as well, either as part of the sensor, if applicable, or as a separate device. Examples include oxygen sensors, pH sensors, blood pressure monitors, breath constituent monitors, blood constituent monitors, heart rate monitors and depth of anesthesia monitors.

The nasal alar sensors described herein may also be used in combination with other PPG sensors, including those designed for emplacement at the nose (e.g., nasal alar, nasal septum and bridge of the nose), lip, cheek, tongue or a selected site at the ear (e.g., ear canal, concha, pinnae, scaphoid fossa, or ear lobe), forehead, fingers and toes. Description of monitoring two or more different sites on the body can be found, for example, in U.S. Pat. No. 6,909,912, which is incorporated herein by reference in its entirety. In particular embodiments, a nasal alar sensor described herein may be used with a sensor designed for emplacement at or on the ear. Particular examples of such ear PPG probes can be found in U.S. Pat. Nos. 7,341,559; 5,551,432 and 5,673,692, and in U.S. Patent Publication Nos. 2010/0217103, 2010/0049017, 2010/0331631 and 2009/0275813, the contents of each of which is incorporated herein by reference in its entirety for this purpose. In some cases, it may be useful to place a PPG sensor at a nasal alar site and at an ear site due to the differences in blood flow at the two different sites.

In some embodiments of the present invention, a nasal alar sensor may be included in a system that provides patient feedback when certain PPG signals or certain PPG signal levels are generated. For example, when the sensor is used for respiration monitoring, the PPG sensor may be used with a system that can alert the patient when respiration appears to be irregular or depressed. In particular embodiments, once the PPG signals from the sensor indicate troubled or depressed respiration, the PPG signal processing unit communicates with a device that alerts the patient, e.g., by applying a wisp of air on the cheek (malar region) to stimulate respiration. Other methods of stimulating respiration include tickling the malar region, and application of heat, cold and/or mild electrical stimulation. In some cases, the nasal alar sensors themselves may include a mechanism for alerting the patient. For example, the alar sensor might include a component that provides a wisp of air to the patient's cheek or may provide mild electrical stimulation. In some embodiments, the system may also be configured to alert medical personnel or to take another appropriate action (such as reduction in opiate administration or increased supply of air to an intubated subject), at the time the stimulus is applied and/or when the stimulus does not restore the patient's breathing to acceptable levels.

In the drawings and specification, there have been disclosed embodiments of the invention and, although specific terms are employed, they are used in a generic and descriptive sense only and not for purposes of limitation, the scope of the invention being set forth in the following claims.

We claim:

1. A photoplethysmography (PPG) sensor comprising:
   (a) a clip body comprising a first end portion facing a second end portion, wherein the clip body comprises a first aperture in the first end portion and a second aperture in the second end portion;
   (b) a flex circuit attached or adjacent to the clip body, wherein the flex circuit generally conforms to a curvature of the clip body,
   wherein the flex circuit comprises a light emitter within or adjacent to the first aperture, a light detector within or adjacent to the second aperture, and at least one of a nasal air pressure detector and a nasal air flow detector,
   wherein the light emitter emits at least one of visible, infrared and ultraviolet light, and wherein the light emitter is facing the light detector, which detects the light from the light emitter; and
   (c) a first elastomeric sleeve that envelops a part of the first end portion and a part of the flex circuit attached or adjacent thereto that comprises the light emitter; and a second elastomeric sleeve that envelops at least part of the second end portion and a part of the flex circuit attached or adjacent thereto that comprises the light detector.

2. The PPG sensor of claim 1, wherein no adhesive is present between the clip body and the flex circuit, between the clip body and the first elastomeric sleeve, between the flex circuit and the first elastomeric sleeve, between the clip body and the second elastomeric sleeve, or between the flex circuit and the second elastomeric sleeve.

3. The PPG sensor of claim 1, wherein the first end portion is configured to secure to an external tissue of a nasal alar, and the second end portion is configured to secure to an internal tissue of the nasal alar.

4. The PPG sensor of claim 3, wherein the clip body generally conforms to a curvature of a nasal tissue secured between the first end portion and the second end portion.

5. The PPG sensor of claim 1, wherein the clip body is a flexible molded polymer clip.

6. The PPG sensor of claim 1, wherein the clip body is opaque.

7. The PPG sensor of claim 1, wherein the clip body is U-shaped.

8. The PPG sensor of claim 1, wherein the first and second elastomeric sleeves bind the clip body and the flex circuit together, and no adhesive is present between the clip body and the flex circuit, between the clip body and the elastomeric sleeves or between the flex circuit and the elastomeric sleeves.

9. The PPG sensor of claim 1, wherein the first and second elastomeric sleeves comprise at least one elastomer selected from a group consisting of silicone, polyurethane, polyvinyl chloride and styrene-based copolymers.

10. The PPG sensor of claim 1, wherein a surface of the first and second elastomeric sleeves configured to contact a body tissue is smooth.

11. The PPG sensor of claim 1, wherein the first and second elastomeric sleeves are transparent.

12. The PPG sensor of claim 1, wherein at least one of the first and second elastomeric sleeves comprises an opaque portion and transparent portion.

13. The PPG sensor of claim 12, wherein the at least one of the first and second elastomeric sleeves is opaque except for a transparent window defined therein.

14. The PPG sensor of claim 1, wherein the at least one of a nasal air pressure detector and a nasal air flow detector is not enveloped by the first elastomeric sleeve or the second elastomeric sleeve.

15. The PPG sensor of claim 1, wherein the at least one of a nasal air pressure detector and a nasal air flow detector comprises a thermistor.

16. The PPG sensor of claim 1, wherein the clip body comprises an additional aperture, and the nasal air pressure or nasal air flow detector is within or adjacent to the additional aperture.

17. The PPG sensor of claim 1, wherein the flex circuit is configured to interface, directly or indirectly, with a signal processing device.

18. The PPG sensor of claim 1, wherein at least part of the first end portion is concave and at least part of the second end portion is convex.

19. A system for monitoring a subject, comprising:
a photoplethymography (PPG) sensor that comprises:
(a) a clip body comprising a first end portion facing a second end portion, wherein the clip body comprises an aperture in the first end portion and an aperture on the second end portion;
(b) a flex circuit attached or adjacent to the clip body, wherein the flex circuit generally conforms to a curvature of the clip body,
wherein the flex circuit comprises a light emitter within or adjacent to the first aperture, a light detector within or adjacent to the second aperture, and at least one of a nasal air pressure detector and a nasal air flow detector,
wherein the light emitter emits at least one of visible, infrared and ultraviolet light, and wherein the light emitter is facing the light detector, which detects the light from the light emitter; and
(c) a first elastomeric sleeve that envelops a part of the first end portion and a part of the flex circuit attached or adjacent thereto that comprises the light emitter; and a second elastomeric sleeve that envelops at least part of the second end portion and a part of the flex circuit attached or adjacent thereto that comprises the light detector; and
a computer communicatingly connected to the PPG sensor.

20. The system of claim 19, wherein the computer comprises a processing module configured to process PPG signals from the PPG sensor to determine the respiratory rate of the subject.

21. The system of claim 19, wherein the computer comprises a processing module configured to process PPG signals from the PPG sensor to monitor blood flow in the subject.

22. The system of claim 19, wherein the PPG sensor is configured to secure to a nasal alar of the subject.

* * * * *